US011918689B1

(12) United States Patent
Patel

(10) Patent No.: US 11,918,689 B1
(45) Date of Patent: Mar. 5, 2024

(54) LIQUID CLONIDINE EXTENDED RELEASE COMPOSITION

(71) Applicant: Tris Pharma, Inc., Monmouth Junction, NJ (US)

(72) Inventor: Grishma Patel, East Brunswick, NJ (US)

(73) Assignee: TRIS PHARMA INC, Monmouth Junction, NJ (US)

( * ) Notice: Subject to any disclaimer, the term of this patent is extended or adjusted under 35 U.S.C. 154(b) by 0 days.

(21) Appl. No.: 17/387,517

(22) Filed: Jul. 28, 2021

Related U.S. Application Data

(60) Provisional application No. 63/057,649, filed on Jul. 28, 2020.

(51) Int. Cl.
| | |
|---|---|
| *A61K 9/16* | (2006.01) |
| *A61K 9/00* | (2006.01) |
| *A61K 9/08* | (2006.01) |
| *A61K 31/4168* | (2006.01) |
| *A61K 45/06* | (2006.01) |
| *A61K 47/18* | (2017.01) |
| *A61K 47/22* | (2006.01) |

(52) U.S. Cl.
CPC .......... *A61K 9/1635* (2013.01); *A61K 9/0053* (2013.01); *A61K 9/08* (2013.01); *A61K 9/1647* (2013.01); *A61K 9/1652* (2013.01); *A61K 31/4168* (2013.01); *A61K 45/06* (2013.01); *A61K 47/183* (2013.01); *A61K 47/22* (2013.01)

(58) Field of Classification Search
CPC .............. A61K 31/4168; A61K 9/1635; A61K 9/1647; A61K 9/1652; A61K 9/0053; B01J 39/00; B01J 45/00
See application file for complete search history.

(56) References Cited

U.S. PATENT DOCUMENTS

| | | | |
|---|---|---|---|
| 4,191,693 A | 3/1980 | Brennan | |
| 4,201,211 A | 5/1980 | Chandrasekaran | |
| 4,221,778 A | 9/1980 | Raghunathan | |
| 4,492,450 A | 1/1985 | Watanabe | |
| 4,603,141 A | 7/1986 | Giles | |
| 4,762,709 A | 8/1988 | Sheumaker | |
| 4,996,047 A | 2/1991 | Kelleher | |
| 5,133,974 A | 7/1992 | Paradissis et al. | |
| 5,258,376 A | 11/1993 | Berstein | |
| 5,273,760 A | 12/1993 | Oshlack et al. | |
| 5,275,820 A | 1/1994 | Chang | |
| 5,286,493 A | 2/1994 | Oshlack et al. | |
| 5,288,497 A | 2/1994 | Stanley et al. | |
| 5,296,228 A | 3/1994 | Chang et al. | |
| 5,484,607 A | 1/1996 | Horacek | |
| 5,580,578 A | 12/1996 | Oshlack et al. | |
| 5,869,100 A | 2/1999 | Horacek | |
| 5,874,090 A | 2/1999 | Baker | |
| 5,958,458 A | 9/1999 | Nortling et al. | |
| 5,968,551 A | 10/1999 | Oshlack et al. | |
| 5,980,882 A | 11/1999 | Eichman | |
| 6,001,392 A | 12/1999 | Wen et al. | |
| 6,030,642 A | 2/2000 | Horacek | |
| 6,046,277 A | 4/2000 | Kolter et al. | |
| 6,066,334 A | 5/2000 | Kolter et al. | |
| 6,096,339 A | 8/2000 | Ayer et al. | |
| 6,228,863 B1 | 5/2001 | Palermo et al. | |
| 6,231,936 B1 | 5/2001 | Kozimor | |
| 6,326,027 B1 | 12/2001 | Miller et al. | |
| 6,432,440 B1 | 8/2002 | Watts | |
| 6,500,459 B1 | 12/2002 | Chhabra et al. | |
| 6,627,635 B2 | 9/2003 | Palermo et al. | |
| 6,667,058 B1 | 12/2003 | Goede | |
| 6,696,088 B2 | 2/2004 | Oshlack et al. | |
| 6,960,357 B2 | 11/2005 | Chopra | |
| 7,067,116 B1 | 6/2006 | Bess et al. | |
| 7,070,806 B2 | 7/2006 | Oshlack et al. | |
| 7,125,563 B2 | 10/2006 | Kumbhani et al. | |
| 7,144,587 B2 | 12/2006 | Oshlack et al. | |
| 7,153,497 B2 | 12/2006 | Hughes et al. | |
| 7,611,730 B2 | 11/2009 | Bartholomaus et al. | |
| 7,884,122 B2 | 2/2011 | Hornacek et al. | |
| 8,062,667 B2 | 11/2011 | Mehta | |
| 8,287,903 B2 | 10/2012 | Mehta | |
| 8,623,409 B1 | 1/2014 | Mehta | |
| 9,295,642 B2 | 3/2016 | Tu | |

(Continued)

FOREIGN PATENT DOCUMENTS

| | | |
|---|---|---|
| EP | 2018160 B1 | 12/2011 |
| JP | 62-048618 | 3/1987 |

(Continued)

OTHER PUBLICATIONS

Burgess and Rangel, "Hydroxypyranones, Hydropyridinones, and their Complexes," Advances in Inorganic Chemistry, vol. 60, pp. 167-238 (2008 Elsevier Inc.).
"Addrenex Pharmaceuticals Reaches Milestone with Filing of NDA for First Product, CloniBID, to Treat Hypertension" PR Newswire, Feb. 20, 2008.
"Addrenex Pharmaceuticals Announces Positive Phase III Clinical Results for Clonicel to Treat ADHD" PR Newswire, Sep. 11, 2008.
"Clonidine Extended Release (ER) Oral Suspension", FDA-Approved Product Literature, Rev 00, Nov. 2009.

(Continued)

*Primary Examiner* — Lakshmi S Channavajjala

(74) *Attorney, Agent, or Firm* — Howson & Howson LLP; Cathy A. Kodroff

(57) ABSTRACT

An oral clonidine dosage unit providing a twenty-four hour extended release profile following a single dose administration is provided. The dosage unit comprises a pharmaceutically effective amount of a coated complex comprising clonidine bound to a cationic exchange resin, which is characterized by a twenty-four hour release profile. Dosage units may also provide an immediate release component.

19 Claims, No Drawings

(56) References Cited

U.S. PATENT DOCUMENTS

| | | | |
|---|---|---|---|
| 9,545,399 | B2 | 1/2017 | Mehta |
| 9,675,703 | B2 | 6/2017 | Mehta |
| 9,675,704 | B2 | 6/2017 | Mehta |
| 2002/0132001 | A1 | 9/2002 | Garthwaite et al. |
| 2002/0156133 | A1 | 10/2002 | Bartholamaeus |
| 2003/0004177 | A1 | 1/2003 | Kao et al. |
| 2003/0050620 | A1 | 3/2003 | Odidi et al. |
| 2003/0082230 | A1 | 5/2003 | Baichwal et al. |
| 2003/0099711 | A1 | 5/2003 | Meadows et al. |
| 2004/0022852 | A1 | 2/2004 | Chopra |
| 2004/0062802 | A1 | 4/2004 | Hermelin |
| 2004/0096501 | A1 | 5/2004 | Vaya |
| 2004/0126428 | A1 | 7/2004 | Hughes |
| 2004/0170684 | A1 | 9/2004 | Baichwal et al. |
| 2005/0112201 | A1 | 5/2005 | Baichwal et al. |
| 2005/0118267 | A1 | 6/2005 | Baichwal et al. |
| 2005/0142097 | A1 | 6/2005 | Deepak et al. |
| 2005/0181050 | A1 | 8/2005 | Hirsh et al. |
| 2005/0232986 | A1 | 10/2005 | Brown |
| 2005/0232987 | A1 | 10/2005 | Brown |
| 2005/0232993 | A1 | 10/2005 | Brown |
| 2005/0265955 | A1 | 12/2005 | Raman et al. |
| 2005/0266032 | A1 | 12/2005 | Srinivasan |
| 2006/0024368 | A1 | 2/2006 | Fassihi et al. |
| 2006/0029664 | A1 | 2/2006 | Srinivasan |
| 2006/0057205 | A1 | 3/2006 | Srinivasan |
| 2006/0062838 | A1 | 3/2006 | DiPierro et al. |
| 2006/0134148 | A1 | 6/2006 | Hollenbeck |
| 2006/0134207 | A1 | 6/2006 | Srinivasan |
| 2006/0204587 | A1 | 9/2006 | Kolter |
| 2006/0263431 | A1 | 11/2006 | Maloney |
| 2006/0286174 | A1 | 12/2006 | Raman |
| 2007/0003512 | A1 | 1/2007 | Stockel et al. |
| 2007/0092553 | A1 | 4/2007 | Tengler |
| 2007/0215511 | A1 | 9/2007 | Mehta |
| 2007/0218140 | A1 | 9/2007 | Tanabe et al. |
| 2008/0152709 | A1 | 6/2008 | Bortz |
| 2008/0175910 | A1 | 7/2008 | Andre |
| 2009/0047345 | A9 | 2/2009 | Lenaerts et al. |
| 2009/0264490 | A1 | 10/2009 | Zanella et al. |
| 2010/0166858 | A1 | 7/2010 | Mehta |
| 2012/0015030 | A1 | 1/2012 | Mehta et al. |
| 2012/0148672 | A1 | 6/2012 | Mehta |
| 2014/0093578 | A1 | 4/2014 | Mehta |
| 2014/0127306 | A1 | 5/2014 | Mehta |
| 2014/0287038 | A1 | 9/2014 | Mehta |
| 2014/0287041 | A1 | 9/2014 | Tu |
| 2015/0182469 | A1 | 7/2015 | Mehta |
| 2016/0143846 | A1 | 5/2016 | Tu |
| 2016/0143854 | A1 | 5/2016 | Tu |
| 2019/0015389 | A1* | 1/2019 | Mehta ............... A61K 9/10 |

FOREIGN PATENT DOCUMENTS

| | | |
|---|---|---|
| JP | 62145014 | 6/1987 |
| JP | H02-172912 | 7/1990 |
| JP | H05-279247 | 10/1993 |
| JP | 2003-528910 | 9/2003 |
| JP | 2005-306778 | 11/2005 |
| JP | 2009-500494 | 1/2009 |
| WO | WO-1992/11038 | 7/1992 |
| WO | WO-2003/020242 A1 | 3/2003 |
| WO | WO-2004/067039 A1 | 8/2004 |
| WO | WO-2005/117843 A2 | 12/2005 |
| WO | WO-2006/022996 A2 | 3/2006 |
| WO | WO-2006/101536 A1 | 9/2006 |
| WO | WO-2007/109104 A2 | 9/2007 |

OTHER PUBLICATIONS

1-Acetyl-2-[(2,6-dichlorophenyl)amino ]-4,5-dihydro-1H-imidazole (CuHuChN30, CAS #54707-71-0) Jul. 7, 2005.
2,6-Dichloroaniline (CAS # 608-31-1) Mar. 26, 2005.
Addrenex Pharmaceuticals, Inc., Press Release, "Addrenex Pharmaceuticals Announces Positive Phase III Clinical Results for Clonicel to Treat ADHD: Non-Stimulant Drug Addresses Wide Range of Symptoms of ADHD", Sep. 10, 2008.
Carter, "The Role of Lubricants in Solid Oral Dosage Manufacturing", [retrieved on Apr. 16, 2010] Retrieved from the Internet: URL:http://www.carterpharmaceuticalconsulting.com/articles/role-of-lubricants-in-solid-dosage-manufacturing.html, 2006.
Davies, "Pharmacokinetics and concentration-effect relationships of intravenous and oral clonidine", Clin. Pharmacol. Ther., 21(5):593-601, May 1977 (Abstract).
Ettmayer, "Lessons learned from marketed and investigational prodrugs", Journal of Medicinal Chemistry, 47(10):2393-2404, May 2004.
Fagan et al. "The Clinical Utility of Colidine" U.S. Pharmacist May 2006 5: HS2-HS16.
Flaa and Kjeldsen, Are all hypertensives made equal? Herz, Jun. 2006, vol. 4:323-330.
Fyhrquist F, Comparison of sustained-release and standard preparations of clonidine in essential hypertension, International Journal of Clinical Pharmacology, Therapy, and Toxicology, Dec. 1983, 21(12):634-6 (Abstract Only).
Gerber et al., Antihypertensive pharmacology. The Western Journal of Medicine, May 1980, vol. 132:430-439.
Glass, "Stability Consideration in Liquid Dosage Forms Extemporaneously Prepared from Commercially Available Products", Journal of Pharmacy & Pharmaceutical Sciences, 9(3):398-426, Dec. 2006.
Hajjar and Kotchen,. Trends in prevalence, awareness, treatment, and control of hypertension in the United States, JAMA, Jul. 2003 vol. 290(2): 199-206.
Hermida et al., Administration-time-dependent effects of hypertensive treatment on the circadian pattern of blood pressure. Current Opinion in Nephrology and Hypertension, Sep. 2005, vol. 14:453-459.
Jeong, "Development of Sustained Release Fast-melting Tablets Using Ion Exchange Resin Complexes" Dissertation Submitted to Purdue University, W. Lafayette, Indiana, pp. 92-105, 114, 141, 142, 169, UMI #3210729, Dec. 2005.
Jeong, "Evaluation of Drug Release Properties from Polymer Coated Drug/Ion-Exchange Resin Complexes Using Mathematical Simulation and Their Application into Sustained Oral Drug Delivery", Department of Pharmaceutical Chemistry, University of Kansas, Jun. 16-18, 2005 (Abstract Only).
M. N. Martinez and M. J. Bartholomew, "What Does it Mean? A review of Interpreting and Calculating Different Types of Means and Standard Deviations". Pharmaceutics, Apr. 13, 2017: 9, 14: doi: 10.3390/pharmaceutics9020014, ppl-23.
MacGregor et al., Pharmacokinetics of oral sustained release clonidine in humans, Arzneimittelforschung, 1985, 35(1A):440-6 (Abstract Only).
Martens et al, A clinical study on the prolonged antihypertensive effect of clonidine in a sustained-release capsule formulation, Pharmatherapeutica, 1980; 2(7): 456-61 (Abstract Only).
Nissen et al, Solid Medication Dosage Form Modification at the Bedside and in the Pharmacy of Queensland Hospitals, Journal of Pharmacy Practice and Research, 39(2): 129, (Apr. 2009).
Prisant et al., Novel drug-delivery systems for hypertension, The American Journal of Medicine, Aug. 1992, 93(2a):455-555 (Abstract Only).
Quadir, FDA Excipient Workshop, "Development of High Functionality Excipients for Immediate and Sustained Release Dosage Forms", Sep. 20, 2004.
Schook et al., Overview of clinical trials with urapidil, The American Journal of Cardiology, Aug. 1989, 64(7): 30D-37D (Abstract Only).
Sciele Pharma, Inc., News Release, "Sciele Pharma and Addrenex Announce Initiation of Pivotal Phase III Trials for Clonicel for ADHD", Oct. 30, 2007.
ScienceLab.com, "Material Safety Data Sheet: Clonidine HCl" [Retrieved on Apr. 16, 2012]. Retrieved from the Internet: URL:http//www.sicencelab.com/xMSDS-Clonidine_Hcl-9923511; Oct. 9, 2005.
Shao et al, Effects of Formulation Variables and Post-Compression Curing on Drug Release from a New Sustained-Release Matrix

(56) References Cited

OTHER PUBLICATIONS

Material: Polyvinylacetate-Povidone, Pharmaceutical Development and Technology, 6(2):247-254, (Sep. 2001).
Steger, "Treatment of hypertensive out-patients with a sustained-release dosage form of clonidine: a comparison with standard tablet therapy and long-term follow-up study", Current Medical Research and Opinion, 6:670-676, Jan. 1980.
Testa, "Prodrug research: Futile or fertile", Biochemical Pharmacology, 68:2097-2106, Dec. 2004.
Timmermans and Van Zwieten,. Quantitative structure-activity relationships in centrally acting imidazolidines structurally related to clonidine. Journal of Medicinal Chemistry, Dec. 1977 vol. 20(12): 1636-1644.
TrisPharma, Press Release, "Tris Pharma announces Two NDA Approvals from FDA Including a Pioneering, First-Ever 24 Hour Liquid Sustained Release Product", Dec. 7, 2009.
Van Zwieten, "Pharmacology of centrally acting hypotensive drugs", Br. J. Clin. Pharmac., 10:13S-20S, Feb. 1980.
Wolf-Maier et al., Hypertension treatment and control in five European countries, Canada, and the United States. Hypertension, Jan. 2004, vol. 43:10-17.
QUILLIVANT XR® Approved Labeling, FDA, Revised Jan. 2017.
QUILLICHEW ER® Approved Labeling, FDA, Revised Mar. 2017.
CONCERTA® Approved Labeling, FDA, Revised Jan. 2017.
RITALIN® Approved Labeling, FDA, Revised Nov. 2019.
RITALIN LA® Approved Labeling, FDA, Revised Nov. 2019.
DYANAVEL XR® Oral Suspension Approved Labeling, FDA, Revised May 2017.
ADDERALL® Approved Labeling, FDA, Revised Jan. 2017.
ADDERALL XR® Approved Labeling, FDA, Revised Jul. 2019.
MYDAYIS® Approved Labeling, FDA, Revised Sep. 2019.
NEXICLON XR® Extended-Release Tablets Approved Labeling, FDA, Aug. 2010.
NEXICLON XR® Extended-Release Oral Suspension Approved Labeling, FDA, Aug. 2010.
CATAPRES® Approved Labeling, FDA, Revised Oct. 2009.
CATAPRES-TTS® Approved Labeling, FDA, Revised Oct. 2011.
DIXARIT Product Monograph, Revised Jul. 30, 2012.
KAPVAY® Approved Labeling, FDA, Revised Aug. 2016.
Brickman, Circadian variations of catecholamines and blood pressure in patients with pseudohypoparathyroidism and hypertension. Chronobiologia, 17(1):37-44 (Abstract Only), Jan.-Mar. 1990.
Verlhac, C. et al. "Physicochemical and Microbiological Stability of a New Oral Clonidine Solution for Paediatric Use" *Pharm Technol Hosp Pharm* Apr. 27, 2018; 3(2): 79-90.
Shao et al., "Drug Release from Kollicoat SR30D-Coated Nonpareil Beads: Evaluation of Coating Level, Plasticizer Type, and Curing Condition", AAPS PharmSciTech (Feb. 12, 2002); vol. 3 (Issue 2), article 15 (http://ww.aapspharmascitech.org).
Response filed on Nov. 20, 2012 to the Office Action dated Aug. 20, 2012 issued in U.S. Appl. No. 12/908,796.
Bortz, et al., Office Action dated Aug. 5, 2009, in U.S. Appl. No. 11/959,879, corresponding to U. S. PG-Pub. No. 2008/0152709.
Final Office Action dated Mar. 23, 2016, issued in U.S. Appl. No. 14/090,274.
International Search Report dated Jul. 28, 2014 issued in International Patent Application No. PCT/US2013/071426.
Kathala, U.S. Appl. No. 15/200,625, filed Jul. 1, 2016.
Mehta, U.S. Appl. No. 12/722,857, filed Feb. 12, 2010.
Mehta, U.S. Appl. No. 14/679,427, filed Apr. 6, 2015.
Mehta, U.S. Appl. No. 14/679,438, filed Apr. 6, 2015.
Mehta, U.S. Appl. No. 15/200,617, filed Jul. 1, 2016.
Mehta, U.S. Appl. No. 15/200,786, filed Jul. 1, 2016.
Office Action dated Aug. 20, 2012 issued in U.S. Appl. No. 12/908,796.
Office Action dated Dec. 6, 2017, issued in U.S. Appl. No. 14/090,274.
Final Office Action dated Jan. 13, 2017, issued in U.S. Appl. No. 14/090,274.
Office Action dated Jan. 16, 2015, issued in U.S. Appl. No. 14/090,274.
Final Office Action dated Jan. 2, 2020, issued in U.S. Appl. No. 15/943,903.
Advisory Action dated Jun. 14, 2016, issued in U.S. Appl. No. 14/090,274.
Office Action dated Mar. 14, 2013 issued in U.S. Appl. No. 12/908,796.
Office Action dated Nov. 29, 2018, issued in U.S. Appl. No. 15/943,903.
Response filed on Feb. 26, 2020 to Office Action dated Jan. 2, 2020, issued in U.S. Appl. No. 15/943,903.
Response filed on Jul. 13, 2017 to Office Action dated Jan. 13, 2017, issued in U.S. Appl. No. 14/090,274.
Response filed on Jun. 15, 2015, to Office Action dated Jan. 16, 2015, issued in U.S. Appl. No. 14/090,274.
Response filed on May 16, 2016 to Office Action dated Mar. 23, 2016, issued in U.S. Appl. No. 14/090,274.
Response filed on May 29, 2019 to Office Action dated Nov. 29, 2018, issued in U.S. Appl. No. 15/943,903.
Response filed on Jun. 12, 2013 to the Office Action dated Mar. 14, 2013 issued in U.S. Appl. No. 12/908,796.
Final Office Action dated Nov. 1, 2021, issued in U.S. Appl. No. 15/943,903.
Response filed on Feb. 5, 2021 to Office Action dated Oct. 5, 2020, issued in U.S. Appl. No. 15/943,903.
Office Action dated Oct. 5, 2020, issued in U.S. Appl. No. 15/943,903.
Advisory Action dated Mar. 5, 2020, issued in U.S. Appl. No. 15/943,903.
U.S. Appl. No. 13/457,646, filed Apr. 27, 2012, for "Method for Preparing Liquid Suspensions Containing Coated Drug—Ion Exchange Resin Complexes", Mehta, et al.
U.S. Appl. No. 12/261,349, filed Oct. 30, 2008, for "Scalable Process for Manufacture of Resin Complexes for Pharmaceutical Use", Mehta, et al.
U.S. Appl. No. 13/244,706, filed Sep. 26, 2011, for "Orally Effective Methylphenidate Extended Release Powder and Aqueous Suspension Product", Mehta, et al.
Office Action dated Jan. 13, 2017, issued in U.S. Appl. No. 14/090,274.
Office Action 1 dated Aug. 9, 2012 in counterpart Japanese Patent Application No. 2009-500494, with translation of Notice of Reasons for Rejection.
Office Action 2 dated Mar. 12, 2013 in counterpart Japanese Patent Application No. 2009-500494, with translation of Notice of Reasons for Rejection.
Office Action 3 dated Oct. 1, 2013 in counterpart Japanese Patent Application No. 2009-500494, with translation of Notice of Reasons for Rejection.

\* cited by examiner

LIQUID CLONIDINE EXTENDED RELEASE COMPOSITION

CROSS-REFERENCE TO RELATED APPLICATIONS

This application claims the benefit under 35 USC 119(e) of U.S. provisional patent application 63/057,649, filed Jul. 28, 2020, which is incorporated by reference herein.

BACKGROUND OF THE INVENTION

This relates generally to pharmaceutical compositions containing clonidine, and more specifically, to an extended release liquid composition providing a once-a-day therapeutic effect.

Clonidine (known chemically as N-(2,6-dichlorophenyl)-4,5-dihydro-1H-imidazol-2-amine) is characterized by the structure:

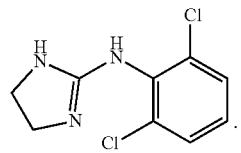

The pharmaceutical product containing the hydrochloride salt of clonidine is commercially available as CATAPRES® (USP from Boehringer Ingelheim Pharmaceuticals, clonidine hydrochloride or 2-(2,6-dichlorophenylamino)-2-imidazoline hydrochloride, MW 266.56). CATAPRES® is a centrally acting alpha-agonist hypotensive agent available in tablet form for oral administration in three dosage strengths: 0.1 mg, 0.2 mg and 0.3 mg. The 0.1 mg tablet is equivalent to 0.087 mg of the free base. Another commercial tablet previously approved for use in the EU is DIXARIT® tablets (clonidine hydrochloride) (used for migraine treatment). The active drug is also available as a transdermal patch (CATAPRES®-TTS), or as an injectable form to be given epidurally, directly to the central nervous system. This drug is useful for treating a number of conditions and may also be used to ease withdrawal symptoms associated with the long-term use of narcotics, alcohol and nicotine (smoking). KAPVAY® brand clonidine hydrochloride (Shinogi Pharma, Inc) is approved for the treatment of attention deficit hyperactivity disorder (ADHD) as a monotherapy or as a adjunctive to stimulant medications. The product is available as an extended release 0.1 mg clonidine (containing clonidine HCl equivalent to 0.087 mg free base) tablet and a 0.2 mg tablet (now discontinued) be taken at bedtime and doses may be adjusted to have a second dose in the morning, to provide a maximum recommended dose of 0.4 mg/day.

Some of the side effects described for clonidine, including lightheadedness, dry mouth, dizziness, or constipation, are believed to be associated with the timing of peak plasma concentrations afforded by the current immediate release formulations. For example, current immediate release clonidine products are administered twice a day, providing two peak plasma concentrations 3-5 hours after each administration. This results in unwanted sedating effects during the day time. When administered orally, dry mouth is also associated with peak plasma concentrations.

An extended release clonidine formulation has been described in U.S. Pat. No. 5,133,974. This document describes formulations comprising a mixture of 0% to about 50% of an immediate release particles comprising a core of at least one drug and up to 100% of an extended release particle which comprises the immediate release particle additionally coated with a dissolution modifying system and optionally an additional drug. US Patent Publication No. 2008/0152709 (Jun. 26, 2009) describes a method for treating a patient with clonidine once daily in a dose of about 0.1 to about 2 mg (based on the weight of the HCl salt form). The composition is described as having a 24-hour profile of plasma clonidine concentration that does not substantially fall below about 0.2 ng/mL and does not substantially exceed about 1 ng/mL. One dosage unit is described as having (a) zero to about 50% by weight of particles comprising clonidine and having an immediate release profile and (b) about 50% to about 100% by weight of particles comprising clonidine and exhibiting an extended release profile. In some embodiments, this dosage form is described as having a peak plasma clonidine concentration of about 4 to about 16 hours after administration. However, the document fails to provide any detailed illustrations of how to formulate clonidine so as to achieve the described release profile.

U.S. Pat. No. 6,030,642, reports that it provides an extended release clonidine formulation in the form of a capsule, which avoids the "peak and trough" side effects of immediate release oral clonidine formulations. The formulation is indicated to be a homogenous mixture of clonidine, one or more cellulose ethers, and one or more inert, pharmaceutically accepted fillers. The binding of drugs on ion exchange particles to achieve sustained release has been described. Clonidine has been described as one drug which could be bound to an ion exchange resin. See, e.g., U.S. Pat. Nos. 5,296,228; 5,275,820; 4,996,047. Liquid suspensions containing coated drug-ion exchange resin complexes and matrices are described in US Published Patent Application No. US-2007-021511-A1 (Sep. 20, 2007). See, also, U.S. Pat. Nos. 8,062,667 and 8,623,409.

There remains a need for methods for stable and effective orally deliverable extended release liquid clonidine compositions useful for treatment of ADHD. There is also a need for orally deliverable pharmaceutical compositions useful in these methods.

SUMMARY OF THE INVENTION

A composition of clonidine which provides a 24-hour profile in a dosage unit which is administered once daily is provided herein. Advantageously, the dosage unit may be administered once daily prior to bedtime or in the morning. Suitably, this may be used as a sole ADHD treatment or in conjunction with other ADHD medications.

In certain embodiments, a twenty-four hour release oral clonidine aqueous suspension is provided which comprises: a pharmaceutically effective amount of barrier coated clonidine-cation exchange resin complex-matrix particles which comprise clonidine bound to a cationic exchange resin in a matrix comprising a hydrophilic polymer or co-polymer; wherein the hydrophilic polymer in the matrix comprises about 5% w/w to about 20% w/w of the particles; wherein the modified release barrier coating comprises of about 50% w/w to about 80% w/w of the particle and is in a layer over the clonidine-cation exchange resin complex-matrix particles; wherein the barrier coating comprises a pH-independent, water-insoluble polymer and a plasticizer and provides modified release to the clonidine in the barrier coated particles, and an aqueous suspension base. In certain embodiments, the suspension is at a pH of about 3 to about 3.5, or pH 3 to 3.5, or pH 3 to 3.2, or values therebetween. In certain embodiments, the suspension further comprises an immediate release clonidine component. In certain embodiments, the immediate release clonidine component comprises an immediate release clonidine-cation exchange resin complex. In certain embodiments, the clonidine composition further comprises clonidine or pharmaceutically acceptable salt. In certain embodiments, the composition comprises uncomplexed cation exchange resin. In certain embodiments, the suspension comprises about 0.1% w/v to about 0.5% w/v of an anti-oxidant, an optionally uncomplexed cation exchange resin, and an optional buffering component. In certain embodiments, a powder-for-suspension or other solid composition is provided which comprises these components in the solid composition. In certain embodiments, the anti-oxidant comprises an ethylene-diamine-tetra-acetic acid or a pharmaceutically acceptable water soluble salt thereof, ethyl maltol, or mixtures thereof. In certain embodiments, the ratio of clonidine to the cation exchange resin in the complex is about 1 parts clonidine by weight to about 25 parts resin by weight to about 1 part clonidine by weight to about 300 parts resin by weight. In certain embodiments, the ratio of clonidine to cation exchange resin in the complex is about 1 parts clonidine by weight to about 150 parts resin by weight. In certain embodiments, the cation exchange resin comprises a sulfonated copolymer of styrene and divinylbenzene and a mobile (exchangeable) cation is sodium with a total cation exchange capacity of about 5 meq/g, and further comprises an average particle size of about 10% to about 25% in the range of 0.075 mm and no more than 1% being greater than 0.150 mm in size, and has about 9.4% to about 11.5% sodium, a potassium exchange capacity of 110 to 135 mg/g, a heavy metals content of less than 10 ppm.

In certain embodiments, the suspension comprises a modified release, barrier coated clonidine-cation exchange resin complex-matrix in which the barrier coating is pH-independent and selected from (a) ethylcellulose and at least one plasticizer; (b) a cured polyvinyl acetate and at least one plasticizer, or (c) a pH-independent acrylate based coating and an optional plasticizer, or (d) mixtures of any of (a), (b), and/or (c). In certain embodiments, the barrier coating comprises about 55% w/w to about 80% w/w of the barrier coated clonidine-cation exchange resin complex-matrix. In certain embodiment, the barrier coating layer comprises about 70% w/w to about 90% w/w polyvinylacetate and about 2.5% w/w to about 20% w/w plasticizer. In certain embodiments, the matrix forming polymer comprises about 5% w/w to about 20% w/w of the barrier clonidine-cation exchange resin complex-matrix, in a water-insoluble polymer. In certain embodiments, the matrix comprises a polyvinylacetate polymer blended with a hydrophilic polymer. In certain embodiments, the matrix comprises a poly(ethyl acrylate-co-methyl methacrylate) 2:1.

In certain embodiments, a method for delivering an effective amount of clonidine for a twenty-four hour period is provided which comprises administering to a subject a single oral dose of a clonidine composition as provided herein. In other embodiments, a method is provided for treating attention deficit hyperactivity disorder (ADHD) by administering to a subject a single oral clonidine composition as provided herein. In certain embodiments, the unit dose comprises 0.1 mg clonidine per mL or 0.2 mg clonidine per mL suspension.

In certain embodiments, a method for treating a patient for attention deficit hyperactivity disorder ADHD comprising administering the suspension as described herein in combination with a second ADHD pharmaceutical composition comprising a different active ingredient, e.g., a methylphenidate, a dexmethylphenidate, or mixtures thereof, or an amphetamine composition.

These and other advantages of the present invention will be readily apparent from the following detailed description of the invention.

DETAILED DESCRIPTION OF THE INVENTION

The present invention provides a clonidine formulation which delivers a 24-hour release therapeutic effect. Due to the prolongation of the drug release and therapeutic effect for up to about 24 hours, the suspensions herein are useful because the once-a-day dose provides a more consistent supply (release) of the clonidine to patients who otherwise may have to take multiple doses a day, thereby exposing those patients to multiple peaks of the drug and unwanted side effects associated with such multiple peaks. This is especially beneficial in the case of small children, elderly people, or others, who have difficulty swallowing larger solid dosage forms such as tablets or capsules.

As used herein, the term "modified release" may refer to a finished composition, a component comprising an active drug in a finished composition, and/or properties of a coating layer or excipient(s). When used in reference to a coating layer, the term "modified release" refers to a coating layer which provides controlled release, extended release or delayed release properties to an active drug coated with modified release coating. Optionally, modified release properties may also be conferred by an excipient, such as one or more matrix-forming component(s). In certain embodiments, a selected modified release component affords an active components having a therapeutic effect over a period of at least about 12 hours to 24-hours. Preferred clonidine compositions are described herein which provide a 24-hour therapeutic effect which comprise a barrier coated, modified release coating over a clonidine-cation exchange resin complex in a matrix which optionally comprises polymers which contribute to the modified release properties of the clonidine. The release profile may be assessed using in vitro dissolution assays known to those of skill in the art [e.g., USP basket method or Paddle Method, or channel flow method]. The release profile can be assessed in vivo (e.g., for bioavailability determinations), using plasma concentrations to assess maximum concentration (Cmax) and area under the curve (AUC). Such assays are well known to those of skill in the art. US Pharmacopeia-National Formulary (USP-NF) 2021.

By "immediate release", it is meant that the formulation containing the therapeutically active agent(s) meets the disintegration and/or dissolution requirements for immediate release of the particular therapeutically active agent(s), as set forth in the USP XXII, 1990 (The United States Pharmacopeia). Generally, the term "immediate release" is the release of an active ingredient from a pharmaceutical formulation where the rate of release of the active pharmaceutical ingredient from the pharmaceutical formulation is not retarded by means of a controlled release matrix or other such means and where the components of the pharmaceutical formulation are designed such that, upon ingestion, maximum exposure of said active pharmaceutical ingredient to body tissues occurs in the minimum period of time. In one embodiment, immediate release provides for at least about 80% of the drug in the immediate release component to be released in less than about one hour following administration to a patient and about 85% of the immediate release drug to be released in about 2 hours following administration to a patient. For example, a drug may release in about 10 minutes to about 45 minutes, or about 30 minutes. In another example, at least about 85%, at least about 90%, at least about 95%, or more, may be released within about 2 hours following administration to a patient.

In one embodiment, a "drug polistirex" is an alternative term for the drug-ion exchange resin complex. The drug polistirex, like the drug-ion exchange resin complex, is optionally with a matrix.

"$C'_{max}$" is the maximum observed plasma concentration, calculated as the mean of the individual maximum blood plasma concentrations.

The term "mean maximum plasma concentration" (mean $C_{max}$) is defined for the purposes of the present invention as the maximum mean plasma concentration.

"Mean plasma concentration" is the arithmetic mean blood plasma concentration.

The term "$T_{max}$" is the time at which the maximum blood plasma concentration ($C_{max}$)s observed for each individual participating in the bioavailability study.

$AUC_{last}$ is the mean area under the plasma concentration-time curve from time 0 to the last with quantifiable concentration. This may be calculated using the log-linear trapezoidal rule that means linear trapezoidal rule up to Tmax, and log trapezoidal rule for the remainder of the curve. See, e.g., M. N. Martinez and M. J. Bartholomew, "What Does it "Mean"? A review of Interpreting and Calculating Different Types of Means and Standard Deviations". Pharmaceutics, 2017: 9, 14: doi:10.3390/pharmaceutics9020014, pp 1-23.

The term "$AUC_{0-Tmax}$" is the mean area under the plasma concentration-time curve from time 0 to $T_{max}$ and is used as an indicator of the rate of drug absorption, or metabolite formation. It is calculated as the arithmetic mean of the area under the plasma concentration-time curve from time 0 to $T_{max}$ calculated for each individual participating in the bioavailability study.

The term "$AUC_{0-\infty}$" or "$AUC_{inf}$" is the mean area under the plasma concentration-time curve extrapolated to infinity. It is calculated as the arithmetic mean of the area under the plasma concentration-time curve from time 0 extrapolated to infinity, calculated for each individual participating in the bioavailability study.

The term "half-life" is the apparent terminal elimination half-life.

The term "HVD" is the half value duration, that is, the time during which clonidine concentrations are above one half the $C'_{max}$. This parameter is an indicator of the shape of the plasma concentration time curve.

The term "immediate release" is the release of an active ingredient from a pharmaceutical formulation where the rate of release of the active pharmaceutical ingredient from the pharmaceutical formulation is not retarded by means of a controlled release matrix or other such means and where the components of the pharmaceutical formulation are designed such that, upon ingestion, maximum exposure of said active pharmaceutical ingredient to body tissues occurs in the minimum period of time.

The term "initial administration" is defined for purposes of the present invention as the first single dose of a formulation containing an active ingredient administered to a patient or subject or the first dose administered to a patient or subject after a suitable washout period.

The words "comprise", "comprises", and "comprising" are to be interpreted inclusively rather than exclusively. The works "consist", "consisting", and its variants, are to be interpreted exclusively, rather than inclusively.

As used herein the term "about" means a variability of 10% from the reference given, unless otherwise specified.

Clonidine-cation exchange resin complexes and matrixes Clonidine, N-(2,6-dichlorophenyl)-4,5-dihydro-1H-imidazol-2-amine, is characterized by the structure:

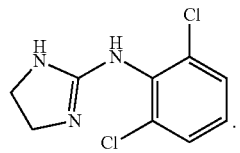 [SMILES: Clc1cccc(Cl)c1NC1=NCCN1]

Clonidine hydrochloride, is an imidazoline derivative and exists as a mesomeric compound. The chemical name is 2-(2,6-dichlorphenylamino)-2-imidazoline hydrochloride. The structural formula is:

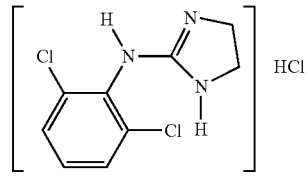

In order to prepare a composition of the invention, one or more salts or one or more prodrugs of clonidine, or in a combination of such forms is used for complexation with a cation exchange resin as described herein. Clonidine in the form of its hydrochloride salt is available commercially.

Cationic exchange resins are readily selected for use as described herein. Cationic exchange resins vary in strength, i.e., in their ability to exchange cations. In one embodiment, a relatively strong cationic resin, e.g., AMBERLITE® IRP69, manufactured by DuPont, a chloride form sytrene-divinylbenzene polymeric (cholestyramine resin) is selected. Alternatively, one may select a relatively weak cationic exchange resin, e.g., AMBERLITE® IRP88 [Dupont], a weakly acidic potassium form cation exchange resin with 4% cross-linked methacrylate (100 to 500 mesh, equiv to about 150 microns to about 27 microns, ASTM standard) or AMBERLITE® 64 (a methacrylic acid and divinylbenzene polymer hydrogen form polacrilex resin, Dupont, purchased with a particle size ranging from 100 to 400 mesh (equiv to 35 microns to 150 microns, ASTM standard size), capacity ~10 meq/g by dry weight). Further, either regularly or irregularly shaped particles may be used as cation exchange resins according to the present invention. Regularly shaped particles are those particles that substantially conform to geometric shapes such as spherical, elliptical, cylindrical and the like, which are exemplified by Dowex® 50W, 50×2, 50×4, or 50×8 (DuPont). Irregularly shaped particles are all particles not considered to be regularly shaped, such as particles with amorphous shapes and particles with increased surface areas due to surface channels or distortions. Irregularly shaped ion-exchange resins of this type are exemplified by AMBERLITE® IRP-69 (DuPont), the use of which is illustrated in the examples below. This cation exchange resin is a sulfonated polymer composed of polystyrene cross-linked with about 8% of divinylbenzene, with an ion-exchange capacity of about 4.5 to 5.5 meq/g of dry resin ($H^+$-form). Another cation exchange resin having similar properties is Dowex® 50WX8 (H$^+$ form, linear formula, $C_{10}H_{12}\cdot C_{10}H_{10}\cdot C_8H_8)_x$, 200-400 mesh particle size, which is equivalent to about 75 microns to about 35 microns, ASTM standard). However, AMBERLITE® IRP-69 consists of irregularly shaped particles with a size range of about 100 to about 500 mesh (about 150 microns to about 27 microns, ASTM standard), whereas the Dowex® 50WX8 is more regularly shaped. Resins are generally purchased with a size ranging from about 25 microns to about 400 microns. However, other sizes may be selected, or larger sized particles may be milled to provide smaller particle sizes.

The suspensions provided herein do not require pretreatment of the pharmaceutical grade cation exchange resin prior to complexing with clonidine. Anti-oxidants are added following the complexation and washing steps, e.g., in the final suspension, to improve storage stability of the final product on storage. Particularly suitable anti-oxidants are also chelating agents and are soluble in the finished aqueous liquid suspension. Such anti-oxidants may include, e.g., disodium edetate, ethyl maltol, amongst other. These antioxidants are described in more detail below. Suitably, the final suspensions contain about 0.1% w/v to about 3% w/v, and more preferably, about 0.2% w/v to about 0.5% w/v.

Binding of clonidine to the cation exchange resin can be accomplished using methods known in the art, e.g., in an aqueous slurry. See, e.g., U.S. Pat. Nos. 8,623,409 and 8,062,667. Once formed, the clonidine-cation exchange resin complex is collected by filtration and washed with appropriate solvents to remove any unbound drug or by-products. The complexes can be air-dried in trays, in a fluid bed dryer, or other suitable dryer, at room temperature or at elevated temperature.

The amount of clonidine that can be loaded onto a resin will typically range from about 0.5% to about 50% by weight of the clonidine-cation exchange resin particles, or about 0.75% to about 1% by weight of the clonidine-cation exchange resin particles. A skilled artisan with limited experimentation can determine the optimum loading for any drug resin complex. In one embodiment, loading of about 10% to about 40% by weight, more desirably, about 15% to about 30% by weight, of the drug-cation exchange resin particles can be employed. Typical loadings of about 25% by weight of the drug-cation exchange resin particles can be advantageously employed.

In one embodiment, the composition of the invention contains clonidine complexed to a sodium polystyrene sulfonate resin in at a ratio of about 1 wt clonidine (based on the weight of the clonidine salt) to about 25 wt resin to about 1 wt clonidine (based on the weight of the clonidine salt) to about 300 wt resin. In another embodiment, the clonidine (based on the weight of the salt) to resin ratio is about 1:120 to about 1:180. In yet a further embodiment, the clonidine to resin ratio is about 1:150.

Granulating Agents and Matrix Forming Polymers

As used herein, the term "matrix forming polymer" or "matrix forming polymeric material" refers to a polymer-based solution which forms a matrix with the clonidine-cation exchange resin complex. This term encompasses both those water-insoluble polymers/co-polymers which function as release retardants as described herein, and hydrophilic polymers/co-polymers which have described in the literature as impregnating or solvating agents. Suitably, the matrix forming polymer is non-reactive polymer with clonidine. In one embodiment, cation exchange resin matrix may include more than one matrix-forming polymer system. For example, a clonidine-cation exchange resin complex matrix may contain both a hydrophilic and a hydrophobic polymer which had been applied, e.g., to facilitate granulation or coating. Such matrix-forming components may be present in an amount of about 5% w/w to about 20% w/w, based on the total weight of the coated clonidine-cation exchange resin complex-matrix. In certain embodiments, the selected matrix-forming polymer systems are admixed with a clonidine-cation exchange resin complex with stirring (i.e., as a granulating agent) to form a clonidine-cation exchange resin complex-matrix.

In one embodiment, a hydrophilic polymer such as polyvinylpyrrolidone [e.g., such as may be purchased commercially as KOLLIDON® 30] is combined with the clonidine-cation exchange resin complex in order to facilitate granulation prior to coating. Other hydrophilic polymers (including co-polymers) may be used as granulating agents and include water-soluble polymeric materials which have been described in the art as impregnating agents or solvating agents and which function in the present application as granulating agents. In one embodiment, the granulating agent is a polyethylene glycol. Examples of desirable impregnating/solvating agents include those described in U.S. patent application Ser. No. 11/724,966, filed Mar. 15, 2007, Published as US 2007-0215511A, Sep. 20, 2007, and Meadows, US 2003-0099711, which are incorporated herein by reference, or in U.S. Pat. No. 4,221,778 and published US Patent application Publication No. US 2003/009971 A1, the disclosures of which are incorporated herein by reference. Specific examples of other impregnating agents include propylene glycol, polyethylene glycol, polyvinyl alcohol, hydroxypropyl methylcellulose, hydroxypropyl cellulose, and sorbitol.

Alternatively, a hydrophobic polymer (and/or copolymer) or a water-insoluble combination of polymers (and/or copolymers) may be selected, such as those which have been described. Such polymers include those which have been previously described as release retardants. As with the other matrix forming polymers, the hydrophobic polymer does not form a separate layer on the clonidine-cation exchange resin complex, but forms a matrix therewith. Examples of suitable release retardants include, for example, a polyvinyl acetate polymer or a mixture of polymers containing same (e.g., KOLLICOAT® SR 30D), cellulose acetates, ethylcellulose polymers (e.g., AQUACOAT™ ECD-30 or SURE-LEASE™), acrylic based polymers or copolymers (e.g., represented by the EUDRAGIT® family of acrylic resins), cellulose phthalate, or any combination of such water-insoluble polymers or polymer systems. These retardants when used may further prolong or alter the release of the drug from the cation exchange resin complex/matrix and maximize attaining the desired release profile. Further, use of a release retardant permit in some cases lowering the amount of coating thickness needed to attain a prolonged drug release of up to 24 hours. These retardants can be used in either substantially pure form or as a commercial preparation obtained from a vendor. The preferred release retardant is a polyvinyl acetate polymer as described herein or an acrylic polymer from the EUDRAGIT® family. Examples of suitable acrylic polymers from the EUDRAGIT® family may include, e.g., a copolymer comprising ethyl acrylate and methyl methacrylate (e.g., EUDRAGIT® NE-30D), or EUDRAGIT® RS, RL30D, RL100, NE, or NM-30D which are largely pH-independent polymers; although less desirable, certain pH-dependent members polymers including, e.g., members of the EUDRAGIT® polymer family, e.g., the L, S, and E, polymers may be selected. EUDRAGIT® NM-30D [Evonik] is an aqueous dispersion of a neutral copolymer based on ethyl acrylate and methyl methacrylate, having an IUPAC name: poly(ethyl acrylate-co-methyl methacrylate) 2:1, with a molecular weight of 600,000 g/mmol. In certain embodiments, about 5% w/w to about 10% w/w of the Poly(ethyl acrylate-co-methyl methacrylate) 2:1 is selected as the granulating agent/matrix forming agent. In certain embodiments, KOLLIDON® SR is a pH-independent polyvinyl acetate and povidone based matrix retarding agent (80% polyvinyl acetate, 19% povidone, 0.8% sodium lauryl sulfate and 0.2% silica). Other mixtures of polyvinyl acetate (e.g., 60% w/w to 90% w/w), polyvinylpyrrolidone (e.g., 15% w/w to 25% w/w), a surfactant(s) (e.g., about 0.5% to 1.5%) and an optional glidant (s) (e.g., about 0.1% w/w to 0.3% w/w) may be selected. In on embodiment, about 5% w/w to about 20% w/w, or 15% w/w to 25% w/w, or about 20% w/w of this blend is selected.

The quantity of a matrix forming polymer is typically in the range of about 3% to about 20% or more by weight to the total weight of the coated clonidine-cation exchange resin complex-matrix. Such a matrix forming polymer is about 3% w/w to about 20%, w/w or about 5% w/w to about 15% w/w, or about 5% w/w to about 10% w/w of the final (dried) coated complex-matrix particle, or about 6% w/w or about 20% w/w, of the final (dried) coated complex-matrix particle. However, higher or lower amounts may be selected.

These matrix forming polymers can be added after a substantial amount of complex formation has taken place. In the more preferred embodiment, the matrix forming polymer is added after the formation of clonidine-cation exchange resin complex. Upon admixing, the clonidine-cation exchange resin complex particles with the matrix polymer (clonidine-cation exchange resin complex-matrix), the mixture is dried and milled appropriately. In some cases, the milling may be carried out before the complete drying of the clonidine-cation exchange resin complex-matrix and then again further drying followed by milling to obtain the desired characteristics. In one embodiment, the clonidine-cation exchange resin complex matrix is milled or passed through a sieve to provide a particle size ranging from about 40 microns to about 410 microns to enhance mouth feel (i.e., texture), or about 50 microns to about 250 microns. These particles may be either regularly or irregularly shaped. This may be performed both prior to and after application of the matrix forming polymer, if any. In some embodiments, the average particle size of the uncoated clonidine-cation exchange resin complex-optional matrix is milled to a size of about 100 to about 200 microns. These particle sizes maybe determined using sieve analysis through sieve shaking having USP standard wire mesh sieves conforming to ASTM specifications.

Following complexation of clonidine and the cation exchange resin, with optional application of matrix forming polymer, water is typically removed from a wet clonidine-cation exchange resin complex or matrix in order to facilitate application of the barrier coating.

Coating System

Suitably, the composition of the invention contains a barrier coating applied over the clonidine-cation exchange resin complex-optional matrix as an aqueous dispersion, dried, and milled or passed through a screen such that the barrier coated clonidine-cation exchange complex and optional matrix in the size range described herein, i.e., in the range of about 50 to about 410 microns. Suitably, the barrier coat is a non-ionic, water-permeable, water-insoluble pH-independent polymer or blend of polymers which provides a modified release profile to the barrier coated clonidine component. In certain embodiments, the barrier coating layer is about 55% to about 80%, by weight, of the total weight of the coated clonidine-cation exchange resin complex-matrix. In another embodiment, the barrier coating layer is about 55% to about 75% by weight of the uncoated clonidine-cation exchange resin complex-matrix, about 55% by weight, about 60% by weight, about 62% by weight, about 65% by weight, about 67% by weight, about 70% by weight, or about 80% by weight, of the total weight of the coated clonidine-cation exchange resin complex-optional matrix.

In one embodiment, the aqueous dispersion is a water insoluble polymer comprising a polyvinyl acetate polymer, or a blend of polymers comprising a polyvinyl acetate polymer. In one embodiment, the barrier coating further contains a plasticizer, which can facilitate uniform coating of the clonidine-cation exchange resin complex-optional matrix and enhances the tensile strength of the barrier coating layer.

One coating composition is applied in the form of an aqueous dispersion containing an polyvinyl acetate (PVA) polymer based aqueous coating dispersion and a plasticizer. The PVA is insoluble in water at room temperature. The PVA may be used in either substantially pure form or as a blend. Where the barrier coating comprises a PVA polymer, the PVA polymer is present in an amount of about 70% to about 90% w/w of the final barrier coating layer, at least about 75%, at least about 80%, about 85% w/w of the final barrier coating layer. Generally, a plasticizer is used in the percent range, or a mixture of plasticizers combine to total about 2 to about 50% by weight of the coating layer, more preferably about 2.5% to about 20% by weight of the coating layer on the coated clonidine-cation exchange resin complex. Preferably a plasticizer is in a range of about 5% to about 20% by weight of the coating layer based on the coated complex provides the most desirable properties. Suitable plasticizers may be water soluble and water insoluble. Examples of suitable plasticizers include, e.g., dibutyl sebacate, propylene glycol, polyethylene glycol, polyvinyl alcohol, triethyl citrate, acetyl triethyl citrate, acetyl tributyl citrate, tributyl citrate, triacetin, and Soluphor® P (2-pyrrolidone), and mixtures thereof. Other plasticizers are described in patent application publication US 2003/0099711 A1, May 29, 2003, page 4 (0041) the disclosure of which is incorporated herein by reference.

A commercial polyvinylacetate blend contains primarily a polyvinyl acetate polymer, a stabilizer, and minor amounts of a surfactant such as sodium lauryl sulfate. Where the barrier coating comprises PVP as the stabilizer component, the final barrier coating layer generally contains about 5 to about 10% w/w of polyvinyl pyrrolidone. In one desired embodiment, the aqueous based barrier coating solution is KOLLICOAT® SR 30 D (BASF Corporation) and whose composition is about 27% PVA polymer, about 2.7% polyvinylpyrrolidone (PVP), about 0.3% sodium lauryl sulfate (solids content 30% w/w), mixed with a plasticizer. See, also, U.S. Pat. Nos. 6,066,334 and 6,026,277, which are incorporated by reference herein. The PVP and surfactant help stabilize the aqueous dispersion of the PVA. Generally, such stabilizing components are present in an amount totaling less than about 10% w/w, and preferably less than about 5% w/w. Optionally, a selected surfactant is present in an amount of about 1% or less. In one embodiment, the surfactant is a non-ionic surfactant. Optionally, an ionic surfactant may be selected.

In a particularly desirable embodiment, the desired modified release is obtained when the coating layer formed by application of the aqueous dispersion containing the KOL- LICOAT® SR-30D polyvinylacetate blend and plasticizer is dried and cured. Preferably, the coating is cured for about 1 to about 24 hours. In alternate embodiments, the coating is cured for about 4 to about 16 hours, and preferably about 5 hours at high temperature, e.g., about 50° C. to about 65° C., and preferably about 60° C. Thus, in one embodiment, the clonidine-cation exchange resin complex-matrix has a cured water-permeable, high tensile strength, water insoluble, barrier coating comprising a non-ionic polymer and a plasticizer and having an elongation factor in the range of about 150% to 400%. In one embodiment, the barrier coating comprises a polyvinyl acetate polymer, a stabilizer, a surfactant and a plasticizer. In one embodiment, a barrier coating comprises about 2.5 to about 10% of plasticizer, about 70 to about 90% polyvinylacetate, about 5 to about 10% polyvinylpyrrolidone, and about 0.1 to about 1% surfactant.

Optionally, another barrier coating may be selected. See, e.g., the barrier coatings described in Kolter et al, U.S. Pat. Nos. 6,066,334 and 6,046,277 and Mehta et al, US Published Patent Application No. US 2007-0215511A, published Sep. 20, 2007, and its counterpart application, WO 2007/109104, which are incorporated herein by reference. See, also, e.g., Wen, U.S. Pat. Nos. 6,046,277 and 6,001,392; Meadows, US Published Patent Application No. 2003/009971 and related application WO 03/020242; Sovereign Pharmaceuticals, WO 2006/022996 and related applications US Published Patent Application Nos. US2005/232986; US2005/232987; US2005/232993; US2005/266032.

Alternatively, other known aqueous or non-aqueous barrier coatings have been described in the literature and/or which are commercially available could be used for the coating process, but are less desirable for the reasons described in US Patent Publication No. US 2007-0215511A and in the literature cited in the background therein. See, e.g., Bess, et al, U.S. Pat. No. 7,067,116; Goede et al, U.S. Pat. No. 6,667,058, Wen et al, U.S. Pat. No. 6,001,392, among others. Such coating materials include ethylcellulose based extended release coatings, e.g., AQUACOAT™ ethylcellulose polymer extended release coating and SURELEASE®. SURELEASE® is available from Colorcon Inc as an aqueous ethyl cellulose dispersion containing water (70.6% w/w), ethylcellulose (18.8% w/w), ammonium hydroxide (4.4% w/w), a medium chain triglyceride (4.0% w/w), and oleic acid (2.2% w/w).

In another embodiment, the coating may be a EUDRAGIT® brand acrylate based coating materials [including, e.g., a poly(ethyl acrylate-co-methyl methacrylate-co-trimethylammonioethyl methacrylate chloride) polymer system]. For example, EUDRAGIT® RS 30D [a pH-independent, 30% aqueous dispersion of poly(ethyl acrylate-co-methyl methacrylate-co-trimethylammonioethyl methacrylate chloride) 1:2:0.1)], or EUDRAGIT® RL 30D [a 30% aqueous dispersion, pH independent polymer, poly(ethyl acrylate-co-methyl methacrylate-co-trimethylammonioethyl methacrylate chloride) 1:2:0.2)] may be selected as the barrier coating. Typically, talc is added to these coatings to address issues associated with tackiness during processing and these coatings are not cured.

Following coating, the coating is dried and is cured. The coating is typically cured for about 1 to about 24 hours. In alternate embodiments, the coating is cured for about 4 to about 16 hours, and preferably about 5 hours at high temperature, e.g., about 50° C. to about 65° C., and preferably about 60° C.

The formulations are designed to provide a once-a-day administrable, 24-hour effective dose, having a single peak in its release profile. In certain embodiments, the compositions are taken at night prior to bed.

In one embodiment, an oral clonidine liquid suspension composition comprising a once-a-day modified release formulation, which is not affected by food. The extended release clonidine composition comprises a pharmaceutically effective amount of a coated complex comprising clonidine bound to a cationic exchange resin (optionally in a matrix) which provides a mean plasma concentration in human patients of about 0.5 ng/mL at about 6 to about 10 hours following a single clonidine dose of about 0.2 mg. The composition may be in the form of a liquid suspension or a tablet. In one embodiment, the plasma half-life of clonidine following a single dose of the composition of the invention is about 10 to about 18 hours.

Finished Dose Formulations

The clonidine-cation exchange resin complex-optional matrix is formulated with pharmaceutically acceptable excipients according to methods well known to those of skill in the art. In certain embodiments, the aqueous liquid suspension are with a pH of about 3 to about 3.5, or a pH of 3 to 3.5, or a pH of 3 to 3.2, or values therebetween. In certain embodiments, the suspensions contain at least one barrier coated clonidine-cation exchange resin complex-matrix. The suspension may further comprise one or more immediate release clonidine components. Such an immediate release component is a clonidine or a pharmaceutically acceptable salt thereof which is uncomplexed to an ion exchange resin, an immediate release clonidine-cation exchange resin complex (uncoated with a modified release barrier coating), or a combination thereof. In certain embodiments, the suspensions further comprise a buffering agent which assists in maintaining the pH with the desired range. Suitable buffers may include, e.g., citric acid, citric acid and sodium citrate, amongst others.

In certain embodiments, an excess of a pharmaceutically acceptable cation exchange resin is admixed into the finished composition. In certain embodiments, free cation exchange resin is included in the suspension when no uncomplexed immediate release component is included in the composition.

The clonidine-cation exchange resin complex-optional matrix composition thus prepared may be stored for future use or promptly formulated with conventional pharmaceutically acceptable carriers to prepare finished ingestible compositions for delivery orally, nasogastric tube, or via other means. The compositions preferentially take the form of aqueous liquid preparations such as suspensions. However, in certain embodiments, a powder for suspension (POS) or other solid oral preparations such as capsules, tablets, caplets, sublinguals, powders, wafers, strips, gels, including liquigels, etc. may be prepared. In one embodiment, a tablet of the invention is formulated as an orally disintegrating or chewable tablet. Such orally dissolving tablets may disintegrate in the mouth in less than about 60 seconds.

Additionally, the barrier coated clonidine-cation exchange resin complex-optional matrix compositions may be formulated using conventional pharmaceutically acceptable carriers or excipients and well established techniques. Without being limited thereto, such conventional carriers or excipients include diluents, binders and adhesives (i.e., cellulose derivatives and acrylic derivatives), lubricants (i.e., magnesium or calcium stearate, or vegetable oils, polyethylene glycols, talc, sodium lauryl sulfate, polyoxy ethylene monostearate), thickeners, solubilizers, humectants, disintegrants, colorants, flavorings, stabilizing agents, sweeteners, and miscellaneous materials such as adsorbents in order to prepare a particular pharmaceutical composition. The stabilizing agents may include preservatives, amongst other components which will be readily apparent to one of ordinary skill in the art.

In certain embodiments, the suspensions contain anti-oxidants, including, pharmaceutically acceptable chelating agents such salts of edetate (also known as salts of ethylenediaminetetraacetic acid, or EDTA, such as disodium EDTA) and/or a 3-hydroxy-4-pyranone such as ethyl maltol.

As used herein, the term "3-hydroxy-4-pyranone" refers to a compound having the structure: wherein each R is independently selected from the group consisting of hydrogen, and alkyl of from 1 to 6 carbon atoms. In one embodiment, the alkyl group is an unbranched alkyl group of from 1 to 3 carbon atoms. In one embodiment, the alkyl group is methyl or ethyl. Optionally, a 3-hydroxy-4-pyranone has a single alkyl substituent at either the 2 or 6-position. For example, one suitable compound is 3-hydroxy-2-methyl-4-pyranone, also known as maltol. Another suitable exemplary compound is 2-ethyl-3-hydroxy-4-pyranone, also known as ethyl maltol. In other embodiments, multiple substitutions may be present. For example, a 3-hydroxy-4-pyranone is selected from the group consisting of 3-hydroxy-4-pyranone, 3-hydroxy-2-methyl-4-pyranone (maltol), 3-hydroxy-2-ethyl-4-pyranone (ethyl maltol), and 3-hydroxy-6-methyl-4-pyranone. Still other compounds within this class may be selected. See, e.g., U.S. Pat. No. 5,258,376. These and other 3-hydroxy-4-pyranone compounds may be purchased from commercial sources, or may be produced synthetically. Suitable routes for generating these compounds are described [see, e.g., Burgess and Rangel, "Hydroxypyranones, Hydropyridinones, and their Complexes, Advances in Inorganic Chemistry, Vol. 60, pp. 167-238 (2008 Elsevier Inc.)]. See also, U.S. Pat. No. 4,191,693, incorporated by reference herein which provides methods of synthesis for ethyl maltol. Throughout the following specification and examples, reference is made to ethyl maltol. However, it will be understood that the ethyl maltol may be substituted by maltol or combined with another 3-hydroxy-4-pyranone.

As defined herein, a substantially stable liquid suspension drug product is characterized by maintaining a substantially stable in vitro dissolution release rate pattern from the time of completion of formulation manufacture through the products approved shelf life and a pharmaceutically acceptable drug purity level.

As defined herein, "substantially stable" means that there is less than about 20% variance, less than 10%, 5% variance, more desirably, less than about 3% variance, and still more desirably, less than about 1% variance. In a further embodiment, the composition contains less than about 0.2% of known or unknown degradants, wherein the weight percentage of degradants or byproducts is based on the total starting weight of the active drug.

Without wishing to be bound by theory, inclusion of an antioxidant such as disodium edetate or ethyl maltol or another 3-hydroxy-4-pyranone when the clonidine is in a composition with a cation exchange resin during oxidation conditions and an aqueous composition contributes to reduction in the levels of and/or formation of clonidine degradation products. See, C. Verlhac et al, Pharm Technol Hosp Pharm, 2018: 3(2): 79-90, incorporated by reference herein, for description of certain clonidine degradation products. See, also, European Pharmacopeia. These impurities may include, e.g., Clonidine Related Compound A (25 mg) (1-Acetyl-2-(2,6-dichlorophenylimino)-imidazolidine; CAS #5391-39-9) (CAS 54707-71-); Clonidine Impurity B: 1-Acetyl-2-[(2,6-dichlorophenyl)amino]-4,5-dihydro-1H-imidazole ($C_{11}H_{11}Cl_2N_3O$, CAS #54707-71-0); Clonidine EP Impurity C (2,6-Dichloroaniline; CAS #608-31-1; $C_6H_6Cl_2$—N; Clonidine impurity D; clonidine Impurity E. Thus, the present invention provides a stable liquid suspension containing the clonidine-cation exchange resin complex.

The total amount of anti-oxidants, e.g., disodium edetate and/or amount of 3-hydroxy-4-pyranone compound(s), or mixtures thereof, which prevent undesirable degradation of the drug in the complex and/or another drug in the suspension over the target storage period is considered a "stabilizing amount". In one embodiment, to total anti-oxidants present in an amount of about 0.01% w/v to about 1% w/v of a final liquid suspension product containing the coated clonidine-cation exchange resin complex and any optional immediate release clonidine component.

Suitable thickeners include, e.g., tragacanth; xanthan gum; bentonite; starch; acacia and lower alkyl ethers of cellulose (including the hydroxy and carboxy derivatives of the cellulose ethers). Examples of cellulose include, e.g., hydroxypropyl cellulose, hydroxypropyl methyl cellulose, sodium carboxy methylcellulose, microcrystalline cellulose (MCC), and MCC with sodium carboxyl methyl cellulose. In one embodiment, tragacanth is used and incorporated in an amount of from about 0.1 to about 1.0% weight per volume (w/v) of the composition, and more preferably about 0.5% w/v of the composition. Xanthan gum is used in the amount of from about 0.025 to about 0.5% w/v and preferably about 0.25% w/v. The compositions may include a humectant composition to give the liquid greater viscosity and stability. Suitable humectants useful in the finished formulations include glycerin, polyethylene glycol, propylene glycol and mixtures thereof.

The oral liquid compositions of the present invention may also comprise one or more surfactants in amounts of up to about 5.0% w/v and preferably from about 0.02 to about 3.0% w/v of the total formulation. The surfactants useful in the preparation of the finished compositions of the present invention are generally organic materials which aid in the stabilization and dispersion of the ingredients in aqueous systems for a suitable homogenous composition. Preferably, the surfactants of choice are non-ionic surfactants such as poly(oxyethylene)(20) sorbitan monooleate and sorbitan monooleate. These are commercially known as Tweens and Spans and are produced in a wide variety of structures and molecular weights.

Whereas any one of a number of surfactants may be used, preferably a compound from the group comprising polysorbate copolymers (sorbitan-mono-9-octadecenoate-poly(oxy-1,2-ethanediyl)) is employed. This compound is also added functions to keep any flavors and sweeteners homogeneously dissolved and dispersed in solution.

Suitable polysorbates include polysorbate 20, polysorbate 40, polysorbate 80 and mixtures thereof. Most preferably, polysorbate 80 is employed. The surfactant component will comprise from about 0.01 to about 2.0% w/v of the total composition and preferably will comprise about 0.1% w/v of the total weight of the composition.

A second emulsifier/surfactant useful in combination with polysorbates may be employed and is preferably a poloxamer such as Poloxamer 407. Poloxamer 407 has an HLB (hydrophilic/lipophilic balance) of about 22 and is sold under the tradename PLURONIC®-127 (BASF—NJ). The two surfactants can be employed in substantially equivalent amounts. For example, the Poloxamer 407 and polysorbate 80 may each be employed together at levels of approximately from about 0.02 to about 4.0% w/v of the total weight of the formulation.

Aqueous suspensions may be obtained by dispersing the clonidine-ion exchange resin compositions in a suitable aqueous vehicle, optionally with the addition of suitable viscosity enhancing agent(s) (e.g., cellulose derivatives, xanthan gum, etc). Non-aqueous suspensions may be obtained by dispersing the foregoing compositions in a suitable non-aqueous based vehicle, optionally with the addition of suitable viscosity enhancing agent(s) (e.g., hydrogenated edible fats, aluminum state, etc.). Suitable non-aqueous vehicles include, for example, almond oil, arachis oil, soybean oil or soybean oil or fractionated vegetable oils such as fractionated coconut oil.

Useful preservatives include, but are not limited to, sodium benzoate, benzoic acid, potassium sorbate, parabens (e.g., methyl, ethyl, propyl or butyl-hydroxybenzoates, etc.), and sorbic acid. Amongst useful preservatives include chelating agents some of which are listed above and other chelating agents, e.g., nitrilotriacetic acid (NTA); ethylenediaminetetracetic acid (EDTA), hydroxyethylethylenediaminetriacetic acid (HEDTA), diethylenetriaminepentaacetic acid (DPTA), 1,2-Diaminopropanetetraacetic acid (1,2-PDTA); 1,3-Diaminopropanetetraacetic acid (1,3-PDTA); 2,2-ethylenedioxybis[ethyliminodi(acetic acid)] (EGTA); 1,10-bis(2-pyridylmethyl)-1,4,7,10-tetraazadecane (BPTETA); ethylenediamine (edamine); Trans-1,2-diaminocyclohexane-N, N, N', N'-tetraacetic acid (CDTA); ethylenediamine-N, N'-diacetate (EDDA); phenazine methosulphate (PMS); 2, 6-Dichloro-indophenol (DCPIP); Bis(carboxymethyl)diaza-18-crown-6 (CROWN); porphine; chlorophyll; dimercaprol (2, 3-Dimercapto-1-propanol); citric acid; tartaric acid; fumaric acid; malic acid; and salts thereof. The preservatives listed above are exemplary, but each preservative must be evaluated in each formulation, to assure the compatibility and efficacy of the preservative.

Methods for evaluating the efficacy of preservatives in pharmaceutical formulations are known to those skilled in the art. Preferred preservatives are the paraben preservatives include, e.g., methyl, ethyl, propyl, and butyl paraben. Both methyl and propyl paraben may be present a ratio of methyl paraben to propyl paraben of from about 2.5:1 to about 16:1, preferably 9:1.

In the instance where auxiliary sweeteners are utilized, the present compositions may include those sweeteners well known in the art, including both natural and artificial sweeteners. Thus, additional sweeteners may be chosen from the following non-limiting list: Water-soluble sweetening agents such as monosaccharides, disaccharides and polysaccharides such as xylose, ribose, glucose, mannose, galactose, fructose, dextrose, sucrose, sugar, maltose, partially hydrolyzed starch, or corn syrup solids and sugar alcohols such as sorbitol, xylitol, mannitol and mixtures thereof. In certain embodiments, the compositions provided herein may be free of high fructose corn syrup.

In general, the amount of sweetener will vary with the desired amount of sweeteners selected for a particular liquid formulation. This amount will normally be 0.001 to about 90% by weight, per volume of the final liquid composition, when using an easily extractable sweetener. The water-soluble sweeteners described above, are preferably used in amounts of about 5 to about 70% by weight per volume, and most preferably from about 10 to about 50% by weight per volume of the final liquid composition. In contrast, the artificial sweeteners [e.g., sucralose, acesulfame K, and dipeptide based sweeteners] are used in amounts of about 0.005 to about 5.0% and most preferably about 0.01 to about 2.5% by weight per volume of the final liquid composition. These amounts are ordinarily necessary to achieve a desired level of sweetness independent from the flavor level achieved from flavor oils.

Suitable flavorings include both natural and artificial flavors, and mints such as peppermint, menthol, artificial vanilla, cinnamon, various fruit flavors (e.g., orange), both individual and mixed, essential oils (i.e. thymol, eucylptol, menthol and methyl salicylate) and the like are contemplated. The amount of flavoring employed is normally a matter of preference subject to such factors as flavor type, individual flavor, and strength desired. Thus, the amount may be varied in order to obtain the result desired in the final product. Such variations are within the capabilities of those skilled in the art without the need for undue experimentation. The flavorings are generally utilized in amounts that will vary depending upon the individual flavor, and may, for example, range in amounts of about 0.01 to about 3% by weight per volume of the final composition weight.

The colorants useful in the present invention, include the pigments such as titanium dioxide, that may be incorporated in amounts of up to about 1% by weight per volume, and preferably up to about 0.6% by weight per volume. Also, the colorants may include dyes suitable for food, drug and cosmetic applications, and known as D&C and F.D. & C. dyes and the like. The materials acceptable for the foregoing spectrum of use are preferably water-soluble. Illustrative examples include indigoid dye, known as F.D. & C. Blue No. 2, which is the disodium salt of 5,5'indigotindisulfonic acid. Similarly, the dye known as F.D. & C. Green No. 1 comprises a triphenylmethane dye and is the monosodium salt of 4-[4-N-ethyl p-sulfobenzylamino)diphenylmethylene]-[1-(N-ethyl-N-p-sulfoniumbenzyl)-2,5-cyclohexadienimine]. A full recitation of all F.D. & C. and D. & C. and their corresponding chemical structures may be found in the Kirk-Othmer Encyclopedia of Chemical Technology, in Volume 5, at Pages 857-884, which text is incorporated herein by reference.

Suitable oils and fats that are usable would include partially hydrogenated vegetable or animal fats, such as coconut oil, palm kernel oil, beef tallow, lard, and the like. These ingredients are generally utilized in amounts with respect to the comestible product of up to about 7.0% by weight, and preferably up to about 3.5% by weight of the final product.

Wetting agents also may be employed in the inventive compositions to facilitate the dispersion of any hydrophobic ingredients. The concentration of wetting agents in the composition should be selected to achieve optimum dispersion of the ingredient within the composition with the lowest feasible concentration of wetting agent. It should be appreciated that an excess concentration of wetting agent may cause the composition, as a suspension, to flocculate. Those skilled in the art are well versed in suitable empirical methods to determine the appropriate wetting agents and concentrations to achieve optimum dispersion and avoid flocculation. Suitable wetting agents are listed in the US Pharmacopeia-National Formulary (e.g., USP-NF 2021).

In another aspect, a product containing at least a coated clonidine-ion exchange resin complex-optional matrix of the invention. In some embodiments, the coated clonidine-ion exchange resin complex-optional matrix are in packs in a form ready for administration, e.g., a blister pack, a bottle, syringes, foil packs, sachets pouches, or other suitable container. In other embodiments, the compositions are in concentrated form in packs, optionally with the diluent required to make a final solution for administration. In still other embodiments, the product contains a compound useful in powder form and, optionally, a separate container with a suitable suspension base or other carriers for the drug-cation exchange resin complex.

Uses of Formulations

The formulations described herein are useful for delivering a twenty-four hour extended release profile of clonidine in a single oral dose. Suitably, the method involves administering to a subject a single oral clonidine dosage unit as described herein. In one embodiment, the single oral clonidine dose is administered at bedtime for treatment of attention deficit hyperactivity disorder. In other embodiments, the single oral clonidine dose is administered at bed-time (i.e, at night) for treatment of attention deficit hyperactivity disorder.

Clonidine has been found useful in treatment of a wide range of diseases and disorders, not all of which are known to be mediated by catecholamines or even related to α-adrenergic activity. A list of therapeutic uses of clonidine has been compiled, for example, by Fagan et al. (2006) U.S. Pharmacist 5:HS2-HS16, which is incorporated by reference herein. This and other publications describe diseases or disorders for which clonidine is indicated as including, e.g., circulatory disorders including hypertension and cardiovascular disease related thereto, arrhythmia, myocardial ischemia, atrial fibrillation, congestive heart failure, allodynia, hyperalgesia, neuropathic pain, cancer pain, cluster headache, chronic headache, migraine, postoperative pain, spinal cord injury pain, akathisia, restless legs syndrome, peripheral neuropathy, neuralgia, orofacial pain, diabetic gastroparesis, chronic memory disorders, hypertonia, hyperkinetic movement disorders, Tourette's syndrome, substance withdrawal, manic states, behavioral disorders related to encephalopathy, bipolar disorder, narcolepsy, post-traumatic stress disorder, schizophrenia, sleep disorders, social phobia, hyperthyroidism, growth delay, excessive sweating, hot flashes, trichorrhexis nodosa, and combinations thereof. Clonidine has also been described as being useful to treat pain and/or inflammation in, e.g., US Published Patent Application No. 2009/026449 A1 (Oct. 22, 2009), which describes conditions including, e.g., pain due to a spinal disc herniation (i.e., sciatica), spondilothesis, stenosis, osteoarthritis, carpal/tarsal tunnel syndrome, tendonitis, temporomandibular joint disorder (TMJ) and discogenic back pain and joint pain, as well as pain that accompanies or follows surgery.

In certain embodiments, the clonidine ER liquid suspension provided herein is used as a monotherapy in treating ADHD in pediatric patients aged 6 to 17 or in adult patients aged 18 and older, or other patient age groups, e.g., ages 12 to 18, ages 5 to 12, ages 6 to 12, ages 5 to 15 or ages 5 to 80. A patient may be treated with 0.1 to 0.4 mg/day of the clonidine ER liquid suspension (amount of clonidine determined based on the equivalent to clonidine HCl). Thus, a patient may receive 0.1 mg/day, 0.2 mg/day, 0.3 mg/day, or 0.4 mg/day (e.g., a day is about a 24-hour time period), based on the equivalent to clonidine HCl. In certain embodiments, the product is taken at bedtime. In other embodiments, the product is taken in the morning. Optionally, the product may be taken both at bedtime and in the morning.

In certain embodiments, a liquid suspension may provide the equivalent of 0.1 mg clonidine/1 mL, as determined based on the amount of clonidine equivalent to clonidine HCl. The clonidine in the coated clonidine-cation exchange resin complex may be 100% of the total clonidine (e.g., with the weight based on the equivalent to 0.1 mg clonidine HCl). Optionally, the total clonidine in the composition may be provided by the coated clonidine-cation exchange complex-optional matrix and one or more immediate release components to achieve the desired dose. In such embodiments, the modified release barrier coated clonidine-cation exchange resin complex (optional) matrix provides at least 50% w/w to about 95% w/w of the total clonidine, or about 60% w/w to about 85% w/w of the total clonidine, or about 70% w/w to about 80% w/w of the total clonidine, or about 70% w/w to about 95% w/w, or about 85% to about 95% w/w of the total clonidine, or about 90% w/w to about 100% w/w of the total clonidine In certain embodiments, the immediate release component(s) provide the remaining clonidine, as based on equivalent to clonidine HC), i.e., the equivalent of 5% w/w to about 50% w/w clonidine, or about 10% w/w clonidine to about 35% w/w clonidine, or about 15% w/w to about 25% w/w, as determined based on the amount of clonidine equivalent to clonidine HCl. In certain embodiments, the immediate release component comprises an uncoated clonidine-cation exchange resin complex, an immediate release clonidine (free clonidine or clonidine salt), or a mixture thereof. The uncoated clonidine-cation exchange resin complex may be present in an amount less than, the same as, or more than the free clonidine. Alternatively, the clonidine may be present in an amount less than, the same, or more than the uncoated clonidine-cation exchange resin complex.

In certain embodiments, the clonidine ER liquid suspension is administered in a co-therapy comprising one or more other ADHD products, e.g., methylphenidate, dexmethylphenidate, amphetamine, lisdexamfetamine dimesylate or the like, which may be in liquid or solid form and/or in immediate release or extended release forms. For example, suitable companion products may include, e.g., methylphenidate products such as, e.g., QUILLIVANT XR® liquid suspension or QUILLICHEW® XR tablets, [NextWave, manufactured by Tris Pharma, Inc, Cranbury, NJ] (administered in the morning), Concerta® methylphenidate HCl, RITALIN® methylphenidate HCl. Other suitable products for co-administration with a clonidine ER product as provided herein may include, e.g., DYANAVEL® (amphetamines)[Tris Pharma, Cranbury NJ)], or ADDERALL®, ADDERALL® XR, or MYDAYSIS™ (amphetamine and dextroamphetamine, Takeda Pharmaceutical Company).

Compositions can been prepared and release profiles assessed using a variant of the USP Standard Paddle tester.

In certain embodiments, a liquid suspension is provided which comprises a coated clonidine-cation exchange resin complex-matrix and at least one immediate release component having one or more of the pharmacokinetic parameters for clonidine:

(a) an arithmetic mean Cmax (pg/mL) of about 326 pg/mL to about 508 pg/mL, or about 350 pg/mL to about 450 pg/mL, about 375 pg/mL to about 425 pg/mL, or about 408 pg/mL; and/or (b) an arithmetic mean AUC0-∞ (hr·pg/mL) of about 10,650 hr·pg/mL to about 16,650 hr·pg/mL, or 12,500 hr·pg/mL to about 14,550 hr·pg/mL, or about 13320 hr·pg/mL; and/or (c) an arithmetic mean Tmax (hr) of about 14 hours to 22 hours, or about 15.5 hours to about 20.5 hours, or about 17.5 hours;

as assessed following dosing two times in a day separated by about 12 hours interval, 0.1 mg at each dosing time (i.e. at 0 and 12 hours) to provide a total daily dose of 0.2 mg, based on the amount of clonidine equivalent to clonidine HCl. The study was done in adults who fasted for at least 2 hours before and 2 hours after subsequent dosing.

In certain embodiments, the liquid suspensions provide both extended release and immediate release components, but provide a single plasma concentration peak for clonidine.

The following examples illustrate the compositions of the inventions. These formulations are not limitations on the present invention.

EXAMPLES

Example 1: Aqueous Liquid Suspension Comprising Modified Release (Polyvinyl Acetate) Barrier Coated Clonidine-Cation Exchange Resin in Hydrophilic (Polyvinyl Pyrrolidone) Matrix Particles

| A. Uncoated Clonidine - Cation exchange resin complex |
| --- |
| Ingredients |
| Clonidine HCl |
| Sodium Polystyrene Sulfonate (AMBERLITE ® IRP-69) Cation Exchange Resin |
| Purified Water* |

The clonidine-cation exchange resin complex-matrix is prepared by first adding 80 L of purified water into a vessel and dissolving clonidine HCl therein by continuous mixing in a planetary mixer. A sodium polystyrene sulfonate ion exchange resin (AMBERLITE® IRP-69) is dispersed with continuous mixing to form a slurry and mixing is continued for 60 minutes to permit formation of a clonidine-cation exchange resin complex comprising 1 part by weight clonidine to 150 parts by weight resin based on the weight of the complex. Water from the slurry is removed by filtration. The wet resin complex is rinsed twice using purified water and then dried.

| B. Precoating: Formation of Clonidine - Cation exchange resin complex - matrix |
| --- |
| Ingredients |
| Clonidine - Cation Exchange Resin of Part A |
| Povidone (KOLLIDON ® 30) |
| Purified Water* |

In a separate container, povidone (KOLLIDON® 30) is dissolved into purified water (povidone solution). The povidone solution is then sprayed onto the wet resin complex with continuous mixing in a Fluid bed/Planetary mixer to form a uniform clonidine-resin complex matrix. The resulting matrix granules are dried until the moisture content is in the range of 10 to 20%. These semi-dried granules (clonidine-ion exchange resin complex matrix) are then milled using CO-MIL® brand mill fitted with a 40 mesh screen. The granules are further dried to a moisture content of in the range of about 3% to about 7%. These dried granules are passed through a 40 mesh screen using the CO-MIL® brand mill. The final coated particles contains about 6% w/w povidone, based on the weight of the total coated particles.

| C. Barrier Coated Clonidine - Cation Exchange Resin Complex - Matrix |
| --- |
| Precoated Clonidine - Cation Exchange Resin Matrix of Part B |
| Polyvinyl Acetate dispersion |
| Ingredients |
| KOLLICOAT ® SR 30D)** |
| Triacetin USP |
| Purified Water* |

*Removed during processing,
**contains 30% w/w solids

The coated clonidine-ion exchange resin complex matrix is prepared as follows. The coating solution is prepared by mixing triacetin, purified water and polyvinyl acetate dispersion (purchased commercially as KOLLICOAT® SR-30D, from BASF) in a container. The coating solution is passed through an ASTM standard Sieve No. 40 mesh screen. The coating process is performed in a VECTOR FLM™ fluid bed processor equipped with a Wurster column by applying coating solution to the uncoated clonidine-cation exchange resin matrix prepared as in Part B. The coated clonidine-cation exchange resin complex matrix is then passed through an ASTM standard sieve No. 40 mesh screen and placed in a hot air oven at 60° C. for 5 hours. The cured, barrier coated complex clonidine-cation exchange resin complex-particle is again passed through No. 40 mesh screen (i.e., about 410 microns). The barrier coating layer with 55% w/w of the coated particle.

| D. Finished Suspension | |
| --- | --- |
| Ingredients | Clonidine ER Susp (% w/v) |
| Purified water, USP | 45.00 |
| Polysorbate 80, NF | 0.11 |
| Anhydrous citric acid, USP | 0.20 |
| Edetate disodium, USP | 0.30 |
| Sucrose, NF | 20.00 |
| Instant clearjel, | 2.50 |
| Glycerin, USP | 10.00 |
| Methyl paraben, NF | 0.18 |
| Propyl paraben, NF | 0.02 |
| Xanthan gum, NF | 0.21 |
| Coated Clonidine - Cation Exchange Resin Complex - Matrix of C | eq. to 0.1 mg Clonidine HCl per mL |
| Orange flavor | 0.50 |
| Purified water, USP | QS |

In order to prepare the coated clonidine-cation exchange resin matrix liquid suspension formulation, the purified water and sucrose is added into a main process vessel. In a separate vessel, citric acid, disodium edetate, polysorbate 80 and the coated clonidine-cation exchange resin matrix prepared according to part C of this Example are added and mixed at room temperature (about 25° C.) to 40 C for 1-3 days) prior to combination into the main process vessel. In a separate vessel, Instant Clearjel™ is slowly dispersed using high shear mixer. Separately, Glycerin is weighed and heated to 60-70° C. Propylparaben and methylparaben are added into the heated glycerin (60-70° C.) and mixed until completely dissolved (Paraben Solution). Paraben Solution is cooled down to room temperature and xanthan gum is added (Gum dispersion). The Gum dispersion then ready to be added into the main process vessel. Following combination of all components and mixing slowly, the orange flavor is added. The final suspension is obtained by adjusting the volume using Purified water.

Example 2: Aqueous Liquid Suspension Comprising Modified Release (Polyvinyl Acetate) Barrier Coated Clonidine-Cation Exchange Resin in Hydrophilic (Polyvinyl Pyrrolidone) Matrix Particles

A. Uncoated Clonidine - Cation exchange resin complex

Ingredients

Clonidine HCl
Sodium Polystyrene Sulfonate
(AMBERLITE ® IRP-69) Cation
Exchange Resin
Purified Water*

The clonidine-resin complex matrix is prepared by first adding 80 L of purified water into a vessel and dissolving clonidine HCl therein by continuous mixing in a planetary mixer. A sodium polystyrene sulfonate ion exchange resin (AMBERLITE®IRP-69) is dispersed with continuous mixing to form a slurry and mixing is continued for 60 minutes to permit formation of a clonidine-cation exchange resin complex comprising a drug to resin ratio of about 1 to about 300, based on the weight of the complex. Water from the slurry is removed by filtration. The wet resin complex is rinsed twice using purified water and then dried.

B. Precoating: Formation of Clonidine - Cation exchange resin complex - matrix Ingredients Clonidine - Cation Exchange
Resin of Part A
Povidone (KOLLIDON ® 30)
Purified Water*

In a separate container, povidone (KOLLIDON® 30) is dissolved into purified water (povidone solution). The povidone solution is then sprayed onto the wet resin complex with continuous mixing in Fluid Bed/Planetary mixer to form a uniform clonidine-resin complex matrix. The resulting matrix granules are dried until the moisture content is in the range of 10 to 20%. These semi-dried granules (clonidine-ion exchange resin complex matrix) are then milled using CO-MIL® brand mill fitted with a 40 mesh screen. The granules are further dried to a moisture content of in the range of about 3% to about 7%. These dried granules are passed through a 40 mesh screen using the CO-MIL® brand mill. The final coated particles contains 8% w/w povidone, based on the weight of the total coated particles.

C. Barrier Coated Clonidine - Cation Exchange Resin Complex - Matrix

Ingredients

Precoated Clonidine - Cation
Exchange Resin Matrix of Part B
Polyvinyl Acetate dispersion
(KOLLICOAT ® SR 30D)**

C. Barrier Coated Clonidine - Cation Exchange Resin Complex - Matrix

Ingredients

Triacetin USP
Purified Water*

*Removed during processing,
**contains 30% w/w solids

The coated clonidine-ion exchange resin complex matrix is prepared as follows. The coating solution is prepared by mixing triacetin, purified water and polyvinyl acetate dispersion (purchased commercially as KOLLICOAT® SR-30D, from BASF) in a container. The coating solution is passed through a ASTM standard Sieve No. 40 mesh screen. The coating process is performed in a VECTOR FLM™ fluid bed processor equipped with a Wurster column by applying coating solution to the uncoated clonidine-cation exchange resin matrix prepared as in Part B. The coated clonidine-cation exchange resin complex matrix is then passed through an ASTM standard sieve No. 40 mesh screen and placed in a hot air oven at 60° C. for 5 hours. The cured, barrier coated complex clonidine-cation exchange resin complex-particle is again passed through No. 40 mesh screen (i.e., about 410 microns). The barrier coating layer with 60% w/w of the coated particle.

D. Finished Suspension

| Ingredients | Clonidine ER Susp (% w/v) |
| --- | --- |
| Purified water, USP | 45.00 |
| Polysorbate 80, NF | 0.11 |
| Anhydrous citric acid and sodium citrate, USP | 0.20 |
| Ethyl maltol, USP | 0.30 |
| Sucrose, NF | 20.00 |
| Instant clearjel, | 2.50 |
| Glycerin, USP | 10.00 |
| Methyl paraben, NF | 0.18 |
| Propyl paraben, NF | 0.02 |
| Xanthan gum, NF | 0.21 |
| Coated Clonidine - Cation Exchange Resin Complex - Matrix of C | eq. to 0.1 mg Clonidine HCl per mL |
| Orange flavor | 0.50 |
| Purified water, USP | QS |

In order to prepare the coated clonidine-cation exchange resin matrix liquid suspension formulation, the purified water and sucrose is added into a main process vessel. In a separate vessel, citric acid and sodium citrate, ethyl maltol, polysorbate 80 and the coated clonidine-cation exchange resin matrix prepared according to part C of this Example are added and mixed at room temperature (about 25° C.) to 50° C. for 1 to 3 days prior to combination into the main process vessel. In a separate vessel, Instant Clearjel is slowly dispersed using high shear mixer. Separately, Glycerin is weighed and heated to 60-70° C. Propylparaben and methylparaben are added into the heated glycerin (60-70° C.) and mixed until completely dissolved (Paraben Solution). Paraben Solution is cooled down to room temperature and xanthan gum is added (Gum dispersion). The Gum dispersion then ready to be added into the main process vessel. Following combination of all components and mixing slowly, the orange flavor is added. The final suspension is obtained by adjusting the volume using Purified water.

Example 3: Aqueous Liquid Suspension Comprising Modified Release (Polyvinyl Acetate) Barrier Coated Clonidine-Cation Exchange Resin in Hydrophilic (Polyvinyl Pyrrolidone) Matrix Particles and Immediate Release Component Clonidine-cation exchange resin complex is prepared as described in Example 1A and divided into two portions. A first portion is set aside for combination into the suspension with the coated particles. A second portion of the clonidine-cation exchange resin complex-matrix is further processed to form the matrix and the coated particle as described in Examples 1B and 1C.

Finished Suspension

| Ingredients | Clonidine ER Susp (% w/v) |
|---|---|
| Purified water, USP | 45.00 |
| Polysorbate 80, NF | 0.11 |
| Anhydrous citric acid and sodium citrate, USP | 0.20 |
| Ethyl maltol, USP | 0.30 |
| Sucrose, NF | 20.00 |
| Instant clearjel ™, | 2.50 |
| Glycerin, USP | 10.00 |
| Methyl paraben, NF | 0.18 |
| Propyl paraben, NF | 0.02 |
| Xanthan gum, NF | 0.21 |
| Uncoated Clonidine - Cation Exchange Resin Complex | Equ to 0.05 mg Clonidine HCl per mL |
| Coated Clonidine - Cation Exchange Resin Complex - Matrix | eq. to 0.05 mg Clonidine HCl per mL |
| Orange flavor | 0.50 |
| Purified water, USP | QS |

In order to prepare the coated clonidine-cation exchange resin matrix liquid suspension formulation, the purified water and sucrose is added into a main process vessel. In a separate vessel, citric acid and sodium citrate, ethyl maltol, polysorbate 80, the coated clonidine-cation exchange resin matrix prepared as described in this Example, and uncoated clonidine-cation exchange resin prepared as described in this Example are added and mixed at room temperature for room temperature (about 25° C.) to 50° C. for 1 to 3 days. In a separate vessel, Instant Clearjel™ is slowly dispersed using high shear mixer. Separately, Glycerin is weighed and heated to 60-70° C. Propylparaben and methylparaben are added into the heated glycerin (60-70° C.) and mixed until completely dissolved (Paraben Solution). Paraben Solution is cooled down to room temperature and xanthan gum is added (Gum dispersion). The Gum dispersion then ready to be added into the main process vessel. Following combination of all components and mixing slowly, the orange flavor is added. The final suspension is obtained by adjusting the volume using Purified water.

Example 4: Aqueous Liquid Suspension Comprising Modified Release (Polyvinyl Acetate) Barrier Coated Clonidine-Cation Exchange Resin in Hydrophilic (Polyvinyl Pyrrolidone) Matrix Particles and Immediate Release Component A. Uncoated Clonidine - Cation exchange resin complex Ingredients Clonidine HCl
Sodium Polystyrene Sulfonate
(AMBERLITE ® IRP-69) Cation
Exchange Resin
Purified Water*

The clonidine-cation exchange resin complex-matrix is prepared by first adding 80 L of purified water into a vessel and dissolving clonidine HCl therein by continuous mixing in a planetary mixer. A sodium polystyrene sulfonate ion exchange resin (AMBERLITE® IRP-69) is dispersed with continuous mixing to form a slurry and mixing is continued for 60 minutes to permit formation of a clonidine-cation exchange resin complex comprising 1 part by weight clonidine to 150 parts by weight resin based on the weight of the complex. Water from the slurry is removed by filtration. The wet resin complex is rinsed twice using purified water and then dried.

B. Precoating: Formation of Clonidine - Cation exchange resin complex - matrix

Ingredients

Clonidine - Cation Exchange
Resin of Part A
Povidone (KOLLIDON ® 30)
Purified Water*

In a separate container, povidone (KOLLIDON® 30) is dissolved into purified water (povidone solution). The povidone solution is then sprayed onto the wet resin complex with continuous mixing in a Fluid bed/Planetary mixer to form a uniform clonidine-resin complex matrix. The resulting matrix granules are passed through a 20 mesh screen. The screened granules are dried to a moisture content of in the range of about 3% to about 7%. These dried granules are passed through a 40 mesh screen using the CO-MIL® brand mill. The final coated particles contains about 6% w/w povidone, based on the weight of the total coated particles.

C. Barrier Coated Clonidine - Cation Exchange Resin Complex - Matrix

Ingredients

Precoated Clonidine - Cation
Exchange Resin Matrix of Part B
Polyvinyl Acetate dispersion**
(KOLLICOAT ® SR 30D)
Triacetin USP
Purified Water*

\* Removed during processing,
\*\*contains 30% w/w solids

The coated clonidine-ion exchange resin complex matrix is prepared as follows. The coating solution is prepared by mixing triacetin, purified water and polyvinyl acetate dispersion (purchased commercially as KOLLICOAT® SR-30D, from BASF) in a container. The coating solution is passed through a ASTM standard Sieve No. 40 mesh screen. The coating process is performed in a VECTOR FLM™ fluid bed processor equipped with a Wurster column by applying coating solution to the uncoated clonidine-cation exchange resin matrix prepared as in Part B. The coated clonidine-cation exchange resin complex matrix is then passed through an ASTM standard sieve No. 40 mesh screen and placed in a hot air oven at 60° C. for 5 hours. The cured, barrier coated complex clonidine-cation exchange resin complex-particle is again passed through No. 40 mesh screen (i.e., about 410 microns). The barrier coating layer is applied to achieve a barrier coating weight of about 60% w/w of the coated particle.

| D. Finished Suspension | |
|---|---|
| Ingredients | Clonidine ER Susp (% w/v) |
| Purified water, USP | 45.00 |
| Polysorbate 80, NF | 0.11 |
| Anhydrous citric acid, USP | 0.20 |
| Edetate disodium, USP | 0.30 |
| Sucrose, NF | 20.00 |
| Instant clearjel, | 2.50 |
| Glycerin, USP | 10.00 |
| Methyl paraben, NF | 0.18 |
| Propyl paraben, NF | 0.02 |
| Xanthan gum, NF | 0.21 |
| Clonidine Hydrochloride, USP | eq. to 0.005 mg Clonidine HCl per mL |
| Uncoated Clonidine - Cation Exchange Resin Complex | eq. to 0.005 mg Clonidine HCl per mL |
| Coated Clonidine - Cation Exchange Resin Complex - Matrix of C | eq. to 0.09 mg Clonidine HCl per mL |
| Orange flavor | 0.50 |
| Purified water, USP | QS |

In order to prepare the coated clonidine-cation exchange resin matrix liquid suspension formulation, the purified water and sucrose is added into a main process vessel. In a separate vessel, citric acid, sodium edetate, polysorbate 80, Clonidine Hydrochloride, USP, uncoated Clonidine-cation exchange resin complex (prepared according to part A of this example) and the coated clonidine-cation exchange resin matrix (prepared according to part C of this Example) are added and mixed at room temperature (about 25° C.) to 40° C. for 1-3 days prior to combination into the main process vessel. In a separate vessel, sucrose is dissolved in water and Instant Clearjel is slowly dispersed using high shear mixer. Separately, Glycerin is weighed and heated to 60-70° C. Propylparaben and methylparaben are added into the heated glycerin (60-70° C.) and mixed until completely dissolved (Paraben Solution). Paraben Solution is cooled down to room temperature and xanthan gum is added (Gum dispersion). The Gum dispersion then ready to be added into the main process vessel. Following combination of all components and mixing slowly, the orange flavor is added. The final suspension is obtained by adjusting the volume using Purified water.

Example 5: Aqueous Liquid Suspension Comprising Modified Release (Ethylcellulose) Barrier Coated Clonidine-Cation Exchange Resin in Hydrophilic (Polyvinyl Pyrrolidone) Matrix Particles and Immediate Release Components

| A. Uncoated Clonidine - Cation exchange resin complex |
|---|
| Ingredients |
| Clonidine HCl<br>Sodium Polystyrene Sulfonate<br>(AMBERLITE ™ IRP-69) Cation<br>Exchange Resin<br>Purified Water* |

The clonidine-cation exchange resin complex-matrix is prepared by first adding 80 L of purified water into a vessel and dissolving clonidine HCl therein by continuous mixing in a planetary mixer. A sodium polystyrene sulfonate ion exchange resin (AMBERLITE™ IRP-69) is dispersed with continuous mixing to form a slurry and mixing is continued for 60 minutes to permit formation of a clonidine-cation exchange resin complex comprising 1 part by weight clonidine to 150 parts by weight resin based on the weight of the complex. Water from the slurry is removed by filtration. The wet resin complex is rinsed twice using purified water and then dried.

| B. Precoating: Formation of Clonidine - Cation exchange resin complex - matrix |
|---|
| Ingredients |
| Clonidine - Cation Exchange<br>Resin of Part A<br>Povidone (KOLLIDON ® 30)<br>Purified Water* |

In a separate container, povidone (KOLLIDON® 30) is dissolved into purified water (povidone solution). The povidone solution is then sprayed onto the wet resin complex with continuous mixing in a Fluid bed/Planetary mixer to form a uniform clonidine-resin complex matrix. The resulting matrix granules are passed through a 20 mesh screen. The screened granules are dried to a moisture content of in the range of about 3% to about 7%. These dried granules are passed through a 40 mesh screen using the CO-MIL® brand mill. The final coated particles contains about 6% w/w povidone, based on the weight of the total coated particles.

| C. Barrier Coated Clonidine - Cation Exchange Resin Complex - Matrix |
|---|
| Ingredients |
| Precoated Clonidine - Cation<br>Exchange Resin Matrix of Part B<br>AQUACOAT ™ ECD**<br>ethylcellulose<br>Dibutyl Sebacate NF<br>Purified Water* |

*Removed during processing,
**contains 30% w/w solids

The coated clonidine-ion exchange resin complex matrix is prepared as follows. The coating solution is prepared by mixing dibutyl sebacate, purified water and ethylcellulose dispersion in a container. The coating solution is passed through an ASTM standard Sieve No. 40 mesh screen. The coating process is performed in a VECTOR FLM™ fluid bed processor equipped with a Wurster column by applying coating solution to the uncoated clonidine-cation exchange resin matrix prepared as in Part B. The coated clonidine-cation exchange resin complex matrix is then passed through an ASTM standard sieve No. 40 mesh screen and placed in a hot air oven at 60° C. for 5 hours. The cured, barrier coated complex clonidine-cation exchange resin complex-particle is again passed through No. 40 mesh screen (i.e., about 410 microns). The barrier coating layer is applied to achieve a weight of 70% w/w, 75% w/w or 80% w/w of the coated particle.

| D. Finished Suspension | |
|---|---|
| Ingredients | Clonidine ER Susp (% w/V) |
| Purified water, USP | 45.00 |
| Polysorbate 80, NF | 0.11 |
| Anhydrous citric acid, USP | 0.20 |
| Edetate disodium, USP | 0.30 |
| Sucrose, NF | 20.00 |
| Instant clearjel, | 2.50 |
| Glycerin, USP | 10.00 |
| Methyl paraben, NF | 0.18 |
| Propyl paraben, NF | 0.02 |
| Xanthan gum, NF | 0.21 |
| Clonidine Hydrochloride, USP | eq. to 0.005 mg Clonidine HCl per mL |
| Uncoated Clonidine - Cation Exchange Resin Complex | eq. to 0.005 mg Clonidine HCl per mL |
| Coated Clonidine - Cation Exchange Resin Complex - Matrix of C | eq. to 0.09 mg Clonidine HCl per mL |
| Orange flavor | 0.50 |
| Purified water, USP | QS |

In order to prepare the coated clonidine-cation exchange resin matrix liquid suspension formulation, the purified water and sucrose is added into a main process vessel. In a separate vessel, citric acid, sodium edetate, polysorbate 80, Clonidine Hydrochloride, USP, uncoated Clonidine-cation exchange resin complex (prepared according to part A of this example) and the coated clonidine-cation exchange resin matrix (prepared according to part C of this Example) are added and mixed at room temperature (about 25° C.) to 40° C. for 1-3 days prior to combination into the main process vessel. In a separate vessel, Instant Clearjel™ is slowly dispersed using high shear mixer. Separately, Glycerin is weighed and heated to 60-70° C. Propylparaben and methylparaben are added into the heated glycerin (60-70° C.) and mixed until completely dissolved (Paraben Solution). Paraben Solution is cooled down to room temperature and xanthan gum is added (Gum dispersion). The Gum dispersion then ready to be added into the main process vessel. Following combination of all components and mixing slowly, the orange flavor is added. The final suspension is obtained by adjusting the volume using Purified water.

Example 6: Aqueous Liquid Suspension Comprising Modified Release (Polyvinyl Acetate) Barrier Coated Clonidine-Cation Exchange Resin in Hydrophilic (Polyvinyl Pyrrolidone) Matrix Particles and Immediate Release Component

| A. Uncoated Clonidine - Cation exchange resin complex |
|---|
| Ingredients |
| Clonidine HCl |
| Sodium Polystyrene Sulfonate (AMBERLITE™ IRP-69) Cation Exchange Resin |
| Purified Water* |

The clonidine-cation exchange resin complex-matrix is prepared by first adding 80 L of purified water into a vessel and dissolving clonidine HCl therein by continuous mixing in a planetary mixer. A sodium polystyrene sulfonate ion exchange resin (AMBERLITE™ IRP-69) is dispersed with continuous mixing to form a slurry and mixing is continued for 60 minutes to permit formation of a clonidine-cation exchange resin complex comprising 1 part by weight clonidine to 150 parts by weight resin based on the weight of the complex. Water from the slurry is removed by filtration. The wet resin complex is rinsed twice using purified water and then dried.

| B. Precoating: Formation of Clonidine - Cation exchange resin complex - matrix |
|---|
| Ingredients |
| Clonidine - Cation Exchange Resin of Part A |
| Povidone (KOLLIDON® 30) |
| Purified Water* |

In a separate container, povidone (KOLLIDON® 30) is dissolved into purified water (povidone solution). The povidone solution is then sprayed onto the wet resin complex with continuous mixing in a Fluid bed/Planetary mixer to form a uniform clonidine-resin complex matrix. The resulting matrix granules are passed through a 20 mesh screen. The screened granules are dried to a moisture content of in the range of about 3% to about 7%. These dried granules are passed through a 40 mesh screen using the CO-MIL® brand mill. The final coated particles contains about 6% w/w povidone, based on the weight of the total coated particles.

| C. Barrier Coated Clonidine - Cation Exchange Resin Complex - Matrix |
|---|
| Ingredients |
| Precoated Clonidine - Cation Exchange Resin Matrix of Part B |
| Polyvinyl Acetate dispersion (KOLLICOAT® SR 30D)** |
| Triacetin USP |
| Purified Water* |

*Removed during processing,
**contains 30% w/w solids

The coated clonidine-ion exchange resin complex matrix is prepared as follows. The coating solution is prepared by mixing triacetin, purified water and polyvinyl acetate dispersion (purchased commercially as KOLLICOAT® SR-30D, from BASF) in a container. The coating solution is passed through an ASTM standard Sieve No. 40 mesh screen. The coating process is performed in a VECTOR FLM™ fluid bed processor equipped with a Wurster column by applying coating solution to the uncoated clonidine-cation exchange resin matrix prepared as in Part B. The coated clonidine-cation exchange resin complex matrix is then passed through an ASTM standard sieve No. 40 mesh screen and placed in a hot air oven at 60° C. for 5 hours. The cured, barrier coated complex clonidine-cation exchange resin complex-particle is again passed through No. 40 mesh screen (i.e., about 410 microns). The barrier coating layer is applied to achieve a barrier coating weight of 70% of the coated particle.

D. Finished Suspension

| Ingredients | Clonidine ER Susp (% w/v) |
| --- | --- |
| Purified water, USP | 45.00 |
| Polysorbate 80, NF | 0.11 |
| Anhydrous citric acid, USP | 0.20 |
| Edetate disodium, USP | 0.30 |
| Sucrose, NF | 20.00 |
| Instant clearjel, | 2.50 |
| Glycerin, USP | 10.00 |
| Methyl paraben, NF | 0.18 |
| Propyl paraben, NF | 0.02 |
| Xanthan gum, NF | 0.21 |
| Clonidine Hydrochloride, USP | eq. to 0.005 mg Clonidine HCl per mL |
| Uncoated Clonidine - Cation Exchange Resin Complex | eq. to 0.09 mg Clonidine HCl per mL |
| Coated Clonidine - Cation Exchange Resin Complex - Matrix of C | eq. to 0.005 mg Clonidine HCl per mL |
| Orange flavor | 0.50 |
| Purified water, USP | QS |

In order to prepare the coated clonidine-cation exchange resin matrix liquid suspension formulation, the purified water and sucrose is added into a main process vessel. In a separate vessel, citric acid, sodium edetate, polysorbate 80, Clonidine Hydrochloride, USP, uncoated Clonidine-cation exchange resin complex (prepared according to part A of this example) and the coated clonidine-cation exchange resin matrix (prepared according to part C of this Example) are added and mixed at room temperature (about 25° C.) to 40° C. for 1-3 days prior to combination into the main process vessel. In a separate vessel, Instant Clearjel is slowly dispersed using high shear mixer. Separately, Glycerin is weighed and heated to 60-70° C. Propylparaben and methylparaben are added into the heated glycerin (60-70° C.) and mixed until completely dissolved (Paraben Solution). Paraben Solution is cooled down to room temperature and xanthan gum is added (Gum dispersion). The Gum dispersion then ready to be added into the main process vessel. Following combination of all components and mixing slowly, the orange flavor is added. The final suspension is obtained by adjusting the volume using Purified water.

Example 7: Aqueous Liquid Suspension Comprising Modified Release (Polyvinyl Acetate) Barrier Coated Clonidine-Cation Exchange Resin in Hydrophilic (Polyvinyl Pyrrolidone) Matrix Particles and Immediate Release Component

A. Uncoated Clonidine - Cation exchange resin complex

| Ingredients |
| --- |
| Clonidine HCl |
| Sodium Polystyrene Sulfonate (AMBERLITE™ IRP-69) Cation Exchange Resin |
| Purified Water* |

The clonidine-cation exchange resin complex-matrix is prepared by first adding 80 L of purified water into a vessel and dissolving clonidine HCl therein by continuous mixing in a planetary mixer. A sodium polystyrene sulfonate ion exchange resin (AMBERLITE™ IRP-69) is dispersed with continuous mixing to form a slurry and mixing is continued for 60 minutes to permit formation of a clonidine-cation exchange resin complex comprising 1 part by weight clonidine to 150 parts by weight resin based on the weight of the complex. Water from the slurry is removed by filtration. The wet resin complex is rinsed twice using purified water and then dried.

B. Precoating: Formation of Clonidine - Cation exchange resin complex - matrix

| Ingredients |
| --- |
| Clonidine - Cation Exchange Resin of Part A |
| Povidone (KOLLIDON® 30) |
| Purified Water* |

In a separate container, povidone (KOLLIDON® 30) is dissolved into purified water (povidone solution). The povidone solution is then sprayed onto the wet resin complex with continuous mixing in a Fluid bed/Planetary mixer to form a uniform clonidine-resin complex matrix. The resulting matrix granules are passed through a 20 mesh screen. The screened granules are dried to a moisture content of in the range of about 3% to about 7%. These dried granules are passed through a 40 mesh screen using the CO-MIL® brand mill. The final coated particles contains about 10% w/w povidone, based on the weight of the total coated particles.

C. Barrier Coated Clonidine - Cation Exchange Resin Complex - Matrix

| Ingredients |
| --- |
| Precoated Clonidine - Cation Exchange Resin Matrix of Part B |
| Polyvinyl Acetate dispersion (KOLLICOAT® SR 30D)** |
| Triacetin USP |
| Purified Water* |

*Removed during processing,
**contains 30% w/w solids

The coated clonidine-ion exchange resin complex matrix is prepared as follows. The coating solution is prepared by mixing triacetin, purified water and polyvinyl acetate dispersion (purchased commercially as KOLLICOAT® SR-30D, from BASF) in a container. The coating solution is passed through an ASTM standard Sieve No. 40 mesh screen. The coating process is performed in a VECTOR FLM™ fluid bed processor equipped with a Wurster column by applying coating solution to the uncoated clonidine-cation exchange resin matrix prepared as in Part B. The coated clonidine-cation exchange resin complex matrix is then passed through an ASTM standard sieve No. 40 mesh screen and placed in a hot air oven at 60° C. for 5 hours. The cured, barrier coated complex clonidine-cation exchange resin complex-particle is again passed through No. 40 mesh screen (i.e., about 410 microns). The barrier coating layer is applied to achieve a barrier coating weight of 50% of the coated particle.

D. Finished Suspension

| Ingredients | Clonidine ER Susp (% w/V) |
|---|---|
| Purified water, USP | 45.00 |
| Polysorbate 80, NF | 0.11 |
| Anhydrous citric acid, USP | 0.20 |
| Edetate disodium, USP | 0.30 |
| Sucrose, NF | 20.00 |
| Instant clearjel, | 2.50 |
| Glycerin, USP | 10.00 |
| Methyl paraben, NF | 0.18 |
| Propyl paraben, NF | 0.02 |
| Xanthan gum, NF | 0.21 |
| Clonidine Hydrochloride, USP | eq. to 0.09 mg Clonidine HCl per mL |
| Uncoated Clonidine - Cation Exchange Resin Complex | eq. to 0.005 mg Clonidine HCl per mL |
| Coated Clonidine - Cation Exchange Resin Complex - Matrix of C | eq. to 0.005 mg Clonidine HCl per mL |
| Orange flavor | 0.50 |
| Purified water, USP | QS |

In order to prepare the coated clonidine-cation exchange resin matrix liquid suspension formulation, the purified water and sucrose is added into a main process vessel. In a separate vessel, citric acid, disodium edetate, polysorbate 80, Clonidine Hydrochloride, USP, uncoated Clonidine-cation exchange resin complex (prepared according to part A of this example) and the coated clonidine-cation exchange resin matrix (prepared according to part C of this Example) are added and mixed at room temperature (about 25° C.) to 40° C. for 1-3 days prior to combination into the main process vessel. In a separate vessel, Instant Clearjel is slowly dispersed using high shear mixer. Separately, Glycerin is weighed and heated to 60-70° C. Propylparaben and methylparaben are added into the heated glycerin (60-70° C.) and mixed until completely dissolved (Paraben Solution). Paraben Solution is cooled down to room temperature and xanthan gum is added (Gum dispersion). The Gum dispersion then ready to be added into the main process vessel. Following combination of all components and mixing slowly, the orange flavor is added. The final suspension is obtained by adjusting the volume using Purified water.

Example 8: Aqueous Liquid Suspension Comprising Modified Release (Ethylcellulose) Barrier Coated Clonidine-Cation Exchange Resin in Hydrophilic (Polyvinyl Pyrrolidone) Matrix Particles and Immediate Release Components

A. Uncoated Clonidine - Cation exchange resin complex

| Ingredients |
|---|
| Clonidine HCl |
| Sodium Polystyrene Sulfonate (AMBERLITE ™ IRP-69) Cation Exchange Resin |
| Purified Water* |

The clonidine-cation exchange resin complex-matrix is prepared by first adding 80 L of purified water into a vessel and dissolving clonidine HCl therein by continuous mixing in a planetary mixer. A sodium polystyrene sulfonate ion exchange resin (AMBERLITE™ IRP-69) is dispersed with continuous mixing to form a slurry and mixing is continued for 60 minutes to permit formation of a clonidine-cation exchange resin complex comprising 1 part by weight clonidine to 150 parts by weight resin based on the weight of the complex. Water from the slurry is removed by filtration. The wet resin complex is rinsed twice using purified water and then dried.

B. Precoating: Formation of Clonidine - Cation exchange resin complex - matrix

| Ingredients |
|---|
| Clonidine - Cation Exchange Resin of Part A |
| Povidone (KOLLIDON ® 30) |
| Purified Water* |

In a separate container, povidone (KOLLIDON® 30) is dissolved into purified water (povidone solution). The povidone solution is then sprayed onto the wet resin complex with continuous mixing in a Fluid bed/Planetary mixer to form a uniform clonidine-resin complex matrix. The resulting matrix granules are passed through a 20 mesh screen. The screened granules are dried to a moisture content of in the range of about 3% to about 7%. These dried granules are passed through a 40 mesh screen using the CO-MIL® brand mill. The final coated particles contains about 6% w/w povidone, based on the weight of the total coated particles.

C. Barrier Coated Clonidine - Cation Exchange Resin Complex - Matrix

| Ingredients |
|---|
| Precoated Clonidine - Cation Exchange Resin Matrix of Part B |
| AQUACOAT ™ ECD** |
| ethylcellulose |
| Dibutyl Sebacate NF |
| Purified Water* |

*Removed during processing,
**contains 30% w/w solids

The coated clonidine-ion exchange resin complex matrix is prepared as follows. The coating solution is prepared by mixing dibutyl sebacate, purified water and ethylcellulose dispersion in a container. The coating solution is passed through an ASTM standard Sieve No. 40 mesh screen. The coating process is performed in a VECTOR FLM™ fluid bed processor equipped with a Wurster column by applying coating solution to the uncoated clonidine-cation exchange resin matrix prepared as in Part B. The coated clonidine-cation exchange resin complex matrix is then passed through an ASTM standard sieve No. 40 mesh screen and placed in a hot air oven at 60° C. for 5 hours. The cured, barrier coated complex clonidine-cation exchange resin complex-particle is again passed through No. 40 mesh screen (i.e., about 410 microns). The barrier coating layer is applied to afford a coating weight of 70% w/w, 75% w/w or 80% w/w of the coated particle.

D. Finished Suspension

| Ingredients | Clonidine ER Susp (% w/v) |
| --- | --- |
| Purified water, USP | 45.00 |
| Polysorbate 80, NF | 0.11 |
| Anhydrous citric acid, USP | 0.20 |
| Edetate disodium, USP | 0.30 |
| Sucrose, NF | 20.00 |
| Instant clearjel, | 2.50 |
| Glycerin, USP | 10.00 |
| Methyl paraben, NF | 0.18 |
| Propyl paraben, NF | 0.02 |
| Xanthan gum, NF | 0.21 |
| Clonidine Hydrochloride, USP | eq. to 0.05 mg Clonidine HCl per mL |
| Coated Clonidine - Cation Exchange Resin Complex - Matrix of C | eq. to 0.05 mg Clonidine HCl per mL |
| Orange flavor | 0.50 |
| Purified water, USP | QS |

In order to prepare the coated clonidine-cation exchange resin matrix liquid suspension formulation, the purified water and sucrose is added into a main process vessel. In a separate vessel, citric acid, sodium edetate, polysorbate 80, Clonidine Hydrochloride, USP, uncoated Clonidine-cation exchange resin complex (prepared according to part A of this example) and the coated clonidine-cation exchange resin matrix (prepared according to part C of this Example) are added and mixed at room temperature (about 25° C.) to 40° C. for 1-3 days prior to combination into the main process vessel. In a separate vessel, Instant Clearjel is slowly dispersed using high shear mixer. Separately, Glycerin is weighed and heated to 60-70° C. Propylparaben and methylparaben are added into the heated glycerin (60-70° C.) and mixed until completely dissolved (Paraben Solution). Paraben Solution is cooled down to room temperature and xanthan gum is added (Gum dispersion). The Gum dispersion then ready to be added into the main process vessel. Following combination of all components and mixing slowly, the orange flavor is added. The final suspension is obtained by adjusting the volume using Purified water.

Example 9: Aqueous Liquid Suspension Comprising Modified Release (Ethylcellulose) Barrier Coated Clonidine-Cation Exchange Resin in Hydrophilic (Polyvinyl Pyrrolidone) Matrix Particles Uncoated clonidine-cation exchange resin complex and clonidine-cation exchange resin complex-matrix are prepared as described in Example 1A and 1B, respectively.

Barrier Coated Clonidine - Cation Exchange Resin Complex - Matrix

| Ingredients |
| --- |
| Clonidine - Cation Exchange Resin Matrix of Example 1B |
| AQUACOAT ™ ECD** |
| ethylcellulose |
| Dibutyl Sebacate NF |
| Purified Water* |

*Removed during processing,
**contains 30% w/w solids

The coated clonidine-ion exchange resin complex matrix is prepared as follows. The coating solution is prepared by mixing triacetin, purified water and ethylcellulose (purchased commercially as AQUACOAT®) in a container. The coating solution is passed through a ASTM standard Sieve No. 40 mesh screen. The coating process is performed in a VECTOR FLM™ fluid bed processor equipped with a Wurster column by applying coating solution to the uncoated clonidine-cation exchange resin matrix. The coated clonidine-cation exchange resin complex matrix is then passed through an ASTM standard sieve No. 40 mesh screen and placed in a hot air oven at 60° C. for 5 hours. The cured, barrier coated complex clonidine-cation exchange resin complex-particle is again passed through No. 40 mesh screen (i.e., about 410 microns). The coated particles have a barrier coating layer which comprises 55% w/w to 80% w/w of the coated particle.

Finished Suspension

| Ingredients | Clonidine ER Susp (% w/v) |
| --- | --- |
| Purified water, USP | 45.00 |
| Polysorbate 80, NF | 0.11 |
| Anhydrous citric acid, USP | 0.20 |
| Edetate disodium, USP | 0.30 |
| Sucrose, NF | 20.00 |
| Instant clearjel, | 2.50 |
| Glycerin, USP | 10.00 |
| Methyl paraben, NF | 0.18 |
| Propyl paraben, NF | 0.02 |
| Xanthan gum, NF | 0.21 |
| Coated Clonidine - Cation Exchange Resin Complex - Matrix | eq. to 0.1 mg Clonidine HCl per mL |
| Orange flavor | 0.50 |
| Purified water, USP | QS |

In order to prepare the coated clonidine-cation exchange resin matrix liquid suspension formulation, the purified water and sucrose is added into a main process vessel. In a separate vessel, citric acid, sodium edetate, polysorbate 80 and the coated clonidine-cation exchange resin matrix prepared according to this Example are added and mixed at 40° C. for 1 day prior to combination into the main process vessel. In a separate vessel, Instant Clearjel™ is slowly dispersed using high shear mixer. Separately, Glycerin is weighed and heated to 60-70° C. Propylparaben and methylparaben are added into the heated glycerin (60-70° C.) and mixed until completely dissolved (Paraben Solution). Paraben Solution is cooled down to room temperature and xanthan gum is added (Gum dispersion). The Gum dispersion then ready to be added into the main process vessel. Following combination of all components and mixing slowly, the orange flavor is added. The final suspension is obtained by adjusting the volume using Purified water.

Example 10: Stability Study

A. A Clonidine ER Suspension containing barrier coated clonidine-cation exchange resin matrix, 0.1 mg/mL, and no immediate release component, was prepared as described herein (Test) and assessed in comparison to NEXICLON® ER Oral Suspension, 0.09 mg clonidine per mL (Reference), which was previously approved for use in treating hypertension. A comparison of the chemical stability is provided in the tables below, performed at 1 month, 2 months, 3 months, and 6 months at 40° C., 75% relative humidity (RH):

| Condition Specification Lot No. | Assay 90.0-110.0% | | Preservative Methyl Paraben 50.0-110.0% | | Propyl Paraben 50.0-110.0% | |
|---|---|---|---|---|---|---|
| | Test | Reference | Test | Reference | Test | Reference |
| Initial | 95.7 | 99.1 | 87.4 | 97.7 | 85.8 | 98.2 |
| 1m-40° C./75% RH | 93.1 | 96.4 | 85.9 | 95.0 | 84.0 | 95.0 |
| 2m-40° C./75% RH | NT | 98.6 | NT | 92.7 | NT | 93.7 |
| 3m-40° C./75% RH | 93.1 | 94.2 | 84.2 | 88.9 | 83.2 | 90.5 |
| 6m-40° C./75% RH | 95.5 | 97.6 | 85.3 | 83.4 | 89.8 | 87.9 |

| Condition Specification | pH 2.5-4.0 | |
|---|---|---|
| | Test | Reference |
| Initial | NT | 3.3 |
| 1 m-40° C./75% RH | 3.4 | 3.3 |
| 2 m-40° C./75% RH | NT | 3.2 |
| 3 m-40° C./75% RH | 3.4 | 3.3 |
| 6 m-40° C./75% RH | 3.3 | 3.2 |

| Condition Specification Lot No. | Imp A | Unk | Total | Impurity Imp A NMT 0.50% | Unk NMT 0.83% | Total NMT 2.0% |
|---|---|---|---|---|---|---|
| | | Test | | | Reference | |
| Initial | ND | ND | 0.0 | ND | <QL | 0.0 |
| 1m-40° C./75% RH | ND | ND | 0.0 | ND | 0.42 | 0.4 |
| 2m-40° C./75% RH | NT | NT | NT | ND | 0.50 | 0.5 |
| 3m-40° C./75% RH | ND | ND | 0.0 | ND | 0.38 | 0.4 |
| 6m-40° C./75% RH | ND | 0.16 | 0.2 | ND | 0.64 | 0.9 |

ND—not detected; NT—not tested, <QL—less than quantitation limit, m—month

The following conclusions can be made at the end of 6 months stability under accelerated condition (40° C./75% RH)

Although NEXICLON® (the referenced product) has all results within specifications the current product showed improved chemical stability—this can be concluded based on the total impurity level observed at the end of 6 months.

B. A Clonidine ER Suspension containing barrier coated clonidine-cation exchange resin matrix, 0.1 mg/mL with immediate release clonidine described herein (Test) and assessed in comparison to NEXICLON® ER Oral Suspension, 0.09 mg clonidine per mL (Reference), which was previously approved for use in treating hypertension. A comparison of the chemical stability is provided in the tables below, performed at 1 month, 2 months, 3 months, and 6 months at 40° C., 75% relative humidity (RH):

| Condition Specification Lot | Assay 90.0-110.0% | | Preservative Methyl Paraben 50.0-110.0% | | Propyl Paraben 50.0-110.0% | |
|---|---|---|---|---|---|---|
| | Test | Reference | Test | Reference | Test | Reference |
| Initial | 97.8 | 99.1 | 97.1 | 97.7 | 95.9 | 98.2 |
| 1m-40° C./75% RH | 99.0 | 96.4 | 97.9 | 95.0 | 96.2 | 95.0 |
| 3m-40° C./75% RH | 98.8 | 94.2 | 94.6 | 88.9 | 94.2 | 90.5 |
| 6m-40° C./75& RH | 97.5 | 97.6 | 91.8 | 83.4 | 92.6 | 87.9 |

| Condition Specification Lot | pH 2.5-4.0 | |
|---|---|---|
| | Test | Reference |
| Initial | 3.5 | 3.3 |
| 1 m-40° C./75% RH | 3.5 | 3.2 |
| 3 m-40° C./75% RH | 3.2 | 3.3 |
| 6 m-40° C./75% RH | 3.3 | 3.2 |

| Condition Specification Lot | Imp A NMT 0.50% | Unk NMT 0.83% | Impurity Total NMT 2.0% | Imp A NMT 0.50% | Unk NMT 0.83% | Total NMT 2.0% |
|---|---|---|---|---|---|---|
| | | Test | | | Reference | |
| Initial | ND | ND | 0.0 | ND | <QL | 0.0 |
| 1m-40/75 | ND | ND | 0.0 | ND | 0.42 | 0.4 |
| 3m-40/75 | <QL | 0.23 | 0.4 | ND | 0.38 | 0.4 |
| 6m-40/75 | <QL | <QL | 0.0 | ND | 0.64 | 0.9 |

ND—not detected; <QL—less than quantitation limit, m—month

All patents, patent publications, and other publications listed in this specification are incorporated herein by reference in their entirety. While the invention has been described with reference to a particularly preferred embodiment, it will be appreciated that modifications can be made without departing from the spirit of the invention. Such modifications are intended to fall within the scope of the appended claims.

The invention claimed is:

1. An extended release oral clonidine aqueous suspension which provides a once-a-day therapeutic effect for clonidine comprising:
   (A) a pharmaceutically effective amount of modified release barrier coated clonidine-cation exchange resin complex-matrix particles, wherein the particles each comprise clonidine bound to a cationic exchange resin in a matrix comprising a hydrophilic polymer or co-polymer, wherein the modified release barrier coating comprises 50% w/w to about 80% w/w of the particle and is in a layer over the clonidine-cation exchange resin complex-matrix particles; wherein the modified release barrier coating comprises a pH-independent, water-insoluble polymer and a plasticizer and provides modified release to the clonidine in the barrier coated particles, wherein the hydrophilic polymer in the matrix comprises about 5% w/w to about 20% w/w of the particles:
wherein the modified release barrier coated clonidine-cation exchange resin complex-matrix particles provide about 70% w/w to about 95% w/w of the total clonidine in the suspension, as determined based on the amount of clonidine equivalent to clonidine HCl;
(B) an immediate release clonidine component(s) comprising (1) an immediate release clonidine-cation exchange resin complex- or (2) (a) an immediate release clonidine-cation exchange resin complex and (b) clonidine uncomplexed to an ion exchange resin, a pharmaceutically acceptable salt of clonidine uncomplexed to an ion exchange resin, or a combination thereof, wherein the immediate release clonidine component(s) provide about 5% w/w to about 30% w/w of the total clonidine in the suspension, as determined based on the amount of clonidine equivalent to clonidine HCl;
and
an aqueous suspension base.

2. The extended release oral clonidine aqueous suspension according to claim 1 which further comprises about 0.1% w/v to about 0.5% w/v of an anti-oxidant, and a buffering component.

3. The extended release oral clonidine aqueous suspension according to claim 2, wherein the anti-oxidant comprises an ethylene-diamine-tetra-acetic acid or a pharmaceutically acceptable water soluble salt thereof, ethyl maltol, or mixtures thereof.

4. The extended release oral clonidine aqueous suspension according to claim 1, wherein the immediate release clonidine components comprise the immediate release clonidine-cation exchange resin complex and a pharmaceutically acceptable salt of clonidine uncomplexed to an ion exchange resin.

5. The extended release-oral clonidine aqueous suspension according to claim 1, wherein the ratio of clonidine to cation exchange resin in the complex of (A) and/or (B) is about 1 parts clonidine by weight to about 300 parts resin by weight.

6. The extended-release oral clonidine aqueous suspension according to claim 5, wherein the ratio of clonidine to cation exchange resin in the complex of (A) and/or (B) is about 1 parts clonidine by weight to about 150 parts resin by weight.

7. The extended release oral clonidine aqueous suspension according to claim 5, wherein the ratio of clonidine to cation exchange resin in the complex of (A) and/or (B) is about 1 parts clonidine by weight to about 25 parts resin by weight.

8. The extended release oral clonidine aqueous suspension according to claim 1, wherein the barrier coating is: at least one pH-independent barrier coating of (a) ethylcellulose and at least one plasticizer; (b) a cured polyvinyl acetate and at least one plasticizer, (c) a pH-independent acrylate based coating and an optional plasticizer, or (d) mixtures of any of (a), (b), and/or (c).

9. The extended release oral clonidine aqueous suspension according to claim 8, wherein the barrier coating comprises about 70% w/w to about 90% w/w polyvinyl acetate and about 2.5% w/w to about 20% w/w plasticizer.

10. The extended release oral clonidine aqueous suspension according to claim 1, wherein the barrier coating comprises 49.5% w/w to 60.5% w/w of the coated particles.

11. The extended release oral clonidine aqueous suspension according to claim 1, wherein the hydrophilic polymer or co-polymer in the matrix comprises a polyvinylpyrrolidone.

12. The extended release oral clonidine aqueous suspension according to claim 1, wherein the hydrophilic polymer or co-polymer in the matrix is about 5% w/w to about 10% w/w of the barrier clonidine-cation exchange resin complex-matrix.

13. The extended hour release oral clonidine aqueous suspension according to claim 1, wherein the cation exchange resin of (A) and/or (B) comprises a sulfonated copolymer of styrene and divinylbenzene and a mobile (exchangeable) cation is sodium with a total cation exchange capacity of about 5 meq/g, and further comprises an average particle size of 10% to 25% in the range of 0.075 mm and no more than 1% being greater than 0.150 mm in size, and has about 9.4% to 11.5% sodium, a potassium exchange capacity of 110 to 135 mg/g, a heavy metals content of less than 10 ppm.

14. The extended release oral clonidine aqueous suspension according to claim 1, wherein the suspension provides a single plasma concentration peak for clonidine post-dosing under fasting conditions.

15. The extended release oral clonidine aqueous suspension according to claim 1, wherein the suspension provides one or more of the pharmacokinetic parameters for clonidine of:
(a) an arithmetic mean Cmax (pg/mL) of about 326 pg/mL to about 508 pg/mL; and/or
(b) an arithmetic mean AUC0-∞ (hr-pg/mL) of about 10,650 hr-pg/mL to about 16,650 hr-pg/mL; and/or
(c) an arithmetic mean Tmax (hr) of about 14 hours to 22 hours;
as assessed following dosing two times in a day separated by about 12 hours interval, 0.1 mg clonidine at each dosing time (i.e., at 0 and 12 hours) to provide a total daily dose of 0.2 mg clonidine, based on the equivalent to clonidine HCl.

16. The extended release oral clonidine aqueous suspension according to claim 15, wherein the suspension provides one or more of the pharmacokinetic parameters for clonidine of:
(a) an arithmetic mean Cmax (pg/mL) of about 350 pg/mL to about 450 pg/mL; and/or
(b) an arithmetic mean AUC0-∞ (hr-pg/mL) of about 12,500 hr-pg/mL to about 14,550 hr-pg/mL; and/or
(c) an arithmetic mean Tmax (hr) of about 15.5 hours to about 20.5 hour.

17. A method for delivering an effective amount of clonidine fora twenty-four hour period comprising administering to a subject a single oral clonidine composition according to claim 1 prior to bed time.

18. The extended release oral clonidine aqueous suspension according to claim 1, wherein the suspension is at pH of about 3 to about 3.5.

19. The extended release oral clonidine aqueous suspension according to claim 1, wherein the immediate release clonidine component(s) provide about 10% w/w of the total clonidine in the suspension, as determined based on the amount of clonidine equivalent to clonidine HCl.

* * * * *